(12) United States Patent
Tanoury et al.

(10) Patent No.: US 10,071,979 B2
(45) Date of Patent: Sep. 11, 2018

(54) PROCESS OF PRODUCING CYCLOALKYLCARBOXAMIDO-INDOLE COMPOUNDS

(71) Applicant: Vertex Pharmaceuticals Incorporated, Boston, MA (US)

(72) Inventors: Gerald J. Tanoury, Marlborough, MA (US); Cristian Harrison, Beverly, MA (US); Benjamin Joseph Littler, Carlsbad, CA (US); Peter Jamison Rose, Littleton, MA (US); Robert Michael Hughes, San Diego, CA (US); Young Chun Jung, Lexington, MA (US); David Andrew Siesel, San Diego, CA (US); Elaine Chungmin Lee, Arlington, MA (US); Daniel T. Belmont, Grafton, MA (US); William A. Nugent, Noblesville, IN (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/687,286

(22) Filed: Apr. 15, 2015

(65) Prior Publication Data

US 2015/0218122 A1    Aug. 6, 2015

Related U.S. Application Data

(62) Division of application No. 13/642,642, filed as application No. PCT/US2011/033396 on Apr. 21, 2011, now Pat. No. 9,035,072.

(60) Provisional application No. 61/333,870, filed on May 12, 2010, provisional application No. 61/329,510, filed on Apr. 29, 2010, provisional application No. 61/329,500, filed on Apr. 29, 2010, provisional application No. 61/329,493, filed on Apr. 29, 2010, provisional application No. 61/327,095, filed on Apr. 22, 2010, provisional application No. 61/327,091, filed on Apr. 22, 2010, provisional application No. 61/327,057, filed on Apr. 22, 2010, provisional application No. 61/327,099, filed on Apr. 22, 2010.

(51) Int. Cl.
| | |
|---|---|
| *C07D 209/40* | (2006.01) |
| *C07D 317/46* | (2006.01) |
| *C07D 209/12* | (2006.01) |
| *C07D 317/60* | (2006.01) |
| *C07D 405/12* | (2006.01) |
| *C07C 209/74* | (2006.01) |
| *C07C 225/06* | (2006.01) |

(52) U.S. Cl.
CPC .......... *C07D 317/46* (2013.01); *C07C 209/74* (2013.01); *C07C 225/06* (2013.01); *C07D 209/12* (2013.01); *C07D 317/60* (2013.01); *C07D 405/12* (2013.01)

(58) Field of Classification Search
CPC .................................................. C07D 209/40
USPC .......................................... 548/454, 466, 491
See application file for complete search history.

(56) References Cited

U.S. PATENT DOCUMENTS

| | | |
|---|---|---|
| 4,138,397 A | 2/1979 | Böhme |
| 5,304,121 A | 4/1994 | Sahatjian |
| 5,886,026 A | 3/1999 | Hunter et al. |
| 6,099,562 A | 8/2000 | Ding et al. |
| 6,426,331 B1 | 7/2002 | McKinney et al. |
| 6,479,483 B2 | 11/2002 | Bös et al. |
| 6,770,637 B2 | 8/2004 | Godel et al. |
| 6,777,400 B2 | 8/2004 | Biggadike et al. |
| 6,992,096 B2 | 1/2006 | Karp et al. |
| 7,202,262 B2 | 4/2007 | Karp et al. |
| 7,253,286 B2 | 8/2007 | Funahashi et al. |
| 7,304,080 B2 | 12/2007 | Karp et al. |
| 7,407,976 B2 | 8/2008 | Miller et al. |
| 7,419,991 B2 | 9/2008 | Karp et al. |
| 7,495,103 B2 | 2/2009 | Hadida-Ruah et al. |
| 7,553,855 B2 | 6/2009 | Young et al. |
| 7,582,665 B2 | 9/2009 | Takemoto et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,728,023 B2 | 6/2010 | Takeuchi et al. |
| 7,741,321 B2 | 6/2010 | Hadida Ruah et al. |
| 7,754,739 B2 | 7/2010 | Hadida Ruah et al. |
| 7,772,259 B2 | 8/2010 | Karp et al. |

(Continued)

FOREIGN PATENT DOCUMENTS

| | | |
|---|---|---|
| BR | 10 2012 0254-0 A2 | 10/2014 |
| CA | 2851462 A1 | 7/2004 |

(Continued)

OTHER PUBLICATIONS

Beare, Neil, A., et al. "Palladium-Catalyzed Arylation of Malonates and Cyanoesters Using Sterically Hindered Trialkyl- and Ferrocenyldialkylphosphine Ligands", Journal of Organic Chemistry, American Chemical Society, Easton.; US., vol. 67 (Jan. 1, 2002), pp. 541-555.

(Continued)

*Primary Examiner* — Nyeemah A Grazier
(74) *Attorney, Agent, or Firm* — Finnegan, Henderson, Farabow, Garrett & Dunner, LLP

(57) ABSTRACT

The present invention features processes for preparing compounds, such as (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide (Compound 1), useful for treating CFTR mediated diseases such as cystic fibrosis.

28 Claims, No Drawings

(56) References Cited

U.S. PATENT DOCUMENTS

| | | |
|---|---|---|
| 7,776,905 B2 | 8/2010 | Hadida Ruah et al. |
| 7,846,951 B2 | 12/2010 | Miller et al. |
| 7,893,094 B2 | 2/2011 | Pollard et al. |
| 7,906,516 B2 | 3/2011 | Tsaklakidis et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Hadida Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Hadida Ruah et al. |
| 8,299,099 B2 | 10/2012 | Hadida Ruah et al. |
| 8,314,239 B2 | 11/2012 | Binch et al. |
| 8,314,256 B2 | 11/2012 | Hadida Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Hadida Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Hadida Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Hadida Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Hadida Ruah et al. |
| 8,563,593 B2 * | 10/2013 | Alargova ............... A61K 9/0095 514/414 |
| 8,575,209 B2 | 11/2013 | Hadida Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 * | 12/2013 | Binch ................... C07D 451/02 514/312 |
| 8,604,203 B2 | 12/2013 | Binch et al. |
| 8,609,703 B2 | 12/2013 | Hadida Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Hadida Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar |
| 8,785,640 B2 * | 7/2014 | Binch .................. C07D 451/02 546/126 |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 * | 8/2014 | Keshavarz-Shokri ...................... C07D 405/12 548/454 |
| 8,816,093 B2 | 8/2014 | Siesel |
| 8,822,451 B2 | 9/2014 | Hadida Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Dokou et al. |
| 8,884,018 B2 | 11/2014 | Ambhaikar et al. |
| 8,889,875 B2 | 11/2014 | Hadida Ruah et al. |
| 8,912,199 B2 | 12/2014 | Hadida Ruah et al. |
| 8,952,049 B2 | 2/2015 | Hadida Ruah et al. |
| 8,952,050 B2 | 2/2015 | Hadida Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 * | 5/2015 | Belmont .............. C07D 209/12 548/454 |
| 9,045,425 B2 | 6/2015 | Luisi et al. |
| 9,051,303 B2 * | 6/2015 | Keshavarz-Shokri ...................... C07D 405/12 |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,127,162 B2 | 9/2015 | Harders et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Hadida Ruah et al. |
| 9,241,934 B2 | 1/2016 | Verwijs et al. |
| 9,249,131 B2 | 2/2016 | Hadida Ruah et al. |
| 9,254,291 B2 * | 2/2016 | Looker ................ A61K 31/553 |
| 9,314,455 B2 | 4/2016 | Keshavarz-Shokri et al. |
| 9,321,725 B2 | 4/2016 | Miller et al. |
| 9,351,962 B2 | 5/2016 | Hadida Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,732,080 B2 | 8/2017 | Hadida-Ruah et al. |
| 9,751,839 B2 | 9/2017 | DeMattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,840,499 B2 | 12/2017 | Keshavarz-Shokri et al. |
| 2003/0125315 A1 | 7/2003 | Mjalli et al. |
| 2003/0158188 A1 | 8/2003 | Lee et al. |

(56) References Cited

U.S. PATENT DOCUMENTS

| | | |
|---|---|---|
| 2003/0158198 A1 | 8/2003 | Lee et al. |
| 2003/0219489 A1 | 11/2003 | Curatolo et al. |
| 2004/0105820 A1 | 6/2004 | Weers et al. |
| 2004/0157849 A1 | 8/2004 | Lee et al. |
| 2005/0164973 A1 | 1/2005 | Karp et al. |
| 2005/0070718 A1 | 3/2005 | Lubisch et al. |
| 2005/0113423 A1 | 5/2005 | VanGoor et al. |
| 2005/0113576 A1 | 5/2005 | Lee et al. |
| 2005/0164951 A1 | 7/2005 | Hammock et al. |
| 2005/0215614 A1 | 9/2005 | Singh et al. |
| 2005/0222271 A1 | 10/2005 | Huang |
| 2006/0003005 A1 | 1/2006 | Cao et al. |
| 2006/0004010 A1 | 1/2006 | Habashita et al. |
| 2006/0035943 A1 | 2/2006 | Karp et al. |
| 2006/0148863 A1 | 7/2006 | Karp et al. |
| 2006/0148864 A1 | 7/2006 | Karp et al. |
| 2006/0217448 A1 | 9/2006 | Kelly et al. |
| 2007/0099938 A1 | 5/2007 | Ohmoto et al. |
| 2007/0218138 A1 | 9/2007 | Bittorf et al. |
| 2007/0244159 A1 | 10/2007 | Hadida Ruah et al. |
| 2008/0081814 A1 | 4/2008 | Cezanne et al. |
| 2008/0097083 A1 | 4/2008 | Cho et al. |
| 2008/0132560 A1 | 6/2008 | Chow et al. |
| 2008/0138803 A1 | 6/2008 | Galvan-Goldman (nee Galvan) et al. |
| 2008/0260820 A1 | 10/2008 | Borrelly et al. |
| 2009/0105272 A1 | 4/2009 | Grootenhuis et al. |
| 2009/0131492 A1 | 5/2009 | Ruah et al. |
| 2009/0176839 A1 | 7/2009 | Keshavarz-Shokri et al. |
| 2009/0246820 A1 | 10/2009 | Singh et al. |
| 2009/0270465 A1 | 10/2009 | Albright et al. |
| 2010/0036130 A1 | 2/2010 | Siesel |
| 2010/0074949 A1 | 3/2010 | Rowe et al. |
| 2010/0120789 A1 | 5/2010 | Vicker et al. |
| 2010/0125090 A1 | 5/2010 | Hadida Ruah et al. |
| 2010/0144798 A1 | 6/2010 | VanGoor et al. |
| 2010/0168094 A1 | 7/2010 | Binch et al. |
| 2010/0168158 A1 | 7/2010 | Binch et al. |
| 2010/0249180 A1 | 9/2010 | Gallardo-Godoy |
| 2010/0256184 A1 | 10/2010 | Rowe et al. |
| 2010/0261750 A1 | 10/2010 | Binch et al. |
| 2011/0008259 A1 | 1/2011 | Binch et al. |
| 2011/0046370 A1 | 2/2011 | Sim et al. |
| 2011/0064811 A1 | 3/2011 | Hurter et al. |
| 2011/0098311 A1* | 4/2011 | Van Goor ............ A61K 31/404 514/255.05 |
| 2011/0098484 A1 | 4/2011 | Saitoh et al. |
| 2011/0123449 A1 | 5/2011 | Zhang et al. |
| 2011/0177999 A1 | 7/2011 | Singh et al. |
| 2011/0251253 A1 | 10/2011 | Keshavarz-Shokri et al. |
| 2011/0257196 A1 | 10/2011 | Lu et al. |
| 2011/0257223 A1* | 10/2011 | Goor ............ A61K 31/404 514/304 |
| 2011/0288122 A1 | 11/2011 | Van Goor et al. |
| 2012/0035179 A1 | 2/2012 | Hadida-Ruah et al. |
| 2012/0046330 A1* | 2/2012 | Alargova ............ A61K 9/1623 514/414 |
| 2012/0064157 A1 | 3/2012 | Dokou et al. |
| 2012/0071524 A1 | 3/2012 | Lu et al. |
| 2012/0122921 A1 | 5/2012 | DeMattei et al. |
| 2012/0122922 A1 | 5/2012 | Young et al. |
| 2012/0149708 A1 | 6/2012 | Kashanchi |
| 2012/0177749 A1 | 7/2012 | Tapolsky et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0011923 A1 | 1/2013 | Ruah et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1* | 5/2013 | Van Goor ............ A61K 31/404 514/312 |
| 2013/0143919 A1* | 6/2013 | Van Goor ............ A61K 31/404 514/312 |
| 2013/0158071 A1* | 6/2013 | Van Goor ............ A61K 31/404 514/304 |
| 2013/0172388 A1 | 7/2013 | Xie et al. |
| 2013/0178496 A1 | 7/2013 | Binch et al. |
| 2013/0184276 A1 | 7/2013 | Hadida Ruah et al. |
| 2013/0186801 A1 | 7/2013 | Verwijs |
| 2013/0196983 A1 | 8/2013 | Binch et al. |
| 2013/0197049 A1 | 8/2013 | Li et al. |
| 2013/0224293 A1 | 8/2013 | Dokou et al. |
| 2013/0231364 A1 | 9/2013 | Binch et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0284054 A1 | 10/2013 | Iftime et al. |
| 2013/0284055 A1 | 10/2013 | Belelie et al. |
| 2013/0303484 A1 | 11/2013 | Grootenhuis et al. |
| 2013/0324743 A1* | 12/2013 | Belmont ............... C07D 209/12 548/454 |
| 2013/0331567 A1 | 12/2013 | Hadida-Ruah et al. |
| 2013/0338188 A9* | 12/2013 | Van Goor ............ A61K 31/404 514/312 |
| 2014/0023706 A1 | 1/2014 | Verwijs et al. |
| 2014/0031543 A1 | 1/2014 | Grote et al. |
| 2014/0073667 A1 | 3/2014 | Morgan |
| 2014/0080825 A1 | 3/2014 | Hadida-Ruah et al. |
| 2014/0094499 A1* | 4/2014 | Alargova ............ A61K 9/0095 514/414 |
| 2014/0109899 A1 | 4/2014 | Boucher et al. |
| 2014/0112988 A1 | 4/2014 | Rowe et al. |
| 2014/0121208 A1 | 5/2014 | Van Goor et al. |
| 2014/0142114 A1 | 5/2014 | Meng et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida-Ruah et al. |
| 2014/0158127 A1 | 6/2014 | Boucher et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0228376 A1 | 8/2014 | Bala et al. |
| 2014/0235668 A1 | 8/2014 | Binch et al. |
| 2014/0243289 A1 | 8/2014 | Grootenhuis et al. |
| 2014/0256770 A1 | 9/2014 | DeMattei et al. |
| 2014/0296164 A1 | 10/2014 | Mallon et al. |
| 2014/0302147 A1 | 10/2014 | Hartman et al. |
| 2014/0303204 A1* | 10/2014 | Binch ................... C07D 451/02 514/312 |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0005275 A1 | 1/2015 | Plas et al. |
| 2015/0010628 A1 | 1/2015 | Dokou et al. |
| 2015/0024047 A1 | 1/2015 | Dokou et al. |
| 2015/0031720 A1 | 1/2015 | Gallardo-Godoy |
| 2015/0031722 A1 | 1/2015 | Hadida-Ruah et al. |
| 2015/0045327 A1 | 2/2015 | Van Der Plas et al. |
| 2015/0065487 A1 | 3/2015 | Hadida-Ruah et al. |
| 2015/0065497 A1 | 3/2015 | Hadida Ruah et al. |
| 2015/0065500 A1 | 3/2015 | Hadida-Ruah et al. |
| 2015/0080431 A1* | 3/2015 | Van Goor ............ A61K 31/404 514/312 |
| 2015/0094304 A1 | 4/2015 | Hadida Ruah et al. |
| 2015/0094307 A1 | 4/2015 | Schmidt et al. |
| 2015/0099780 A1 | 4/2015 | Morgan |
| 2015/0119441 A1 | 4/2015 | Hadida Ruah et al. |
| 2015/0126566 A1 | 5/2015 | Hadida-Ruah et al. |
| 2015/0141459 A1* | 5/2015 | Van Goor ............ A61K 31/404 514/312 |
| 2015/0150803 A1 | 6/2015 | Boucher et al. |
| 2015/0150879 A2* | 6/2015 | Van Goor ............ A61K 31/404 514/235.8 |

(56) References Cited

U.S. PATENT DOCUMENTS

| | | | |
|---|---|---|---|
| 2015/0150971 A1 | 6/2015 | Park et al. | |
| 2015/0164881 A1* | 6/2015 | Van Goor | A61K 31/404 514/312 |
| 2015/0164883 A1* | 6/2015 | Van Goor | A61K 31/404 514/312 |
| 2015/0166516 A1 | 6/2015 | Hadida-Ruah et al. | |
| 2015/0174098 A1 | 6/2015 | Hadida Ruah et al. | |
| 2015/0182517 A1 | 7/2015 | Alargova et al. | |
| 2015/0190390 A1 | 7/2015 | Hadida Ruah et al. | |
| 2015/0197744 A1 | 7/2015 | de Boer et al. | |
| 2015/0203478 A1* | 7/2015 | Keshavarz-Shokri | C07D 405/12 514/414 |
| 2015/0209448 A1 | 7/2015 | de Boer et al. | |
| 2015/0231142 A1 | 8/2015 | Van Goor et al. | |
| 2015/0246031 A1 | 9/2015 | Dokou et al. | |
| 2015/0265612 A1 | 9/2015 | Hadida Ruah et al. | |
| 2015/0293078 A1 | 10/2015 | Singh et al. | |
| 2015/0320736 A1 | 11/2015 | Phenix et al. | |
| 2015/0323736 A1* | 11/2015 | Ishida | C03B 37/01222 385/126 |
| 2015/0328217 A1 | 11/2015 | Sandona et al. | |
| 2015/0336898 A1 | 11/2015 | Grootenhuis et al. | |
| 2015/0336956 A1 | 11/2015 | Hadida-Ruah et al. | |
| 2015/0346185 A1 | 12/2015 | Pruliere-Escabasse | |
| 2016/0022633 A1 | 1/2016 | Van Der Plas et al. | |
| 2016/0022664 A2* | 1/2016 | Van Goor | A61K 31/404 514/312 |
| 2016/0022665 A2* | 1/2016 | Van Goor | A61K 31/404 514/312 |
| 2016/0039764 A1 | 2/2016 | Morgan | |
| 2016/0039800 A1 | 2/2016 | Young | |
| 2016/0052916 A1 | 2/2016 | Keshavarz-Shokri et al. | |
| 2016/0067239 A9* | 3/2016 | Van Goor | A61K 31/404 514/312 |
| 2016/0095858 A1 | 4/2016 | Miller et al. | |
| 2016/0096807 A1 | 4/2016 | Strohmeier et al. | |
| 2016/0096835 A1 | 4/2016 | Cole et al. | |
| 2016/0108406 A1 | 4/2016 | McCray et al. | |
| 2016/0120841 A1 | 5/2016 | Kym et al. | |
| 2016/0122331 A1 | 5/2016 | Kym et al. | |
| 2016/0128984 A1 | 5/2016 | Cole et al. | |
| 2016/0143898 A1 | 5/2016 | Hadida Ruah et al. | |
| 2016/0151335 A1 | 6/2016 | Tait et al. | |
| 2016/0166540 A1* | 6/2016 | Looker | H01L 21/76802 514/414 |
| 2016/0200684 A2* | 7/2016 | Van Goor | A61K 31/404 514/312 |
| 2016/0200712 A1 | 7/2016 | Siesel | |
| 2016/0221952 A1 | 8/2016 | Yang et al. | |
| 2016/0221995 A1 | 8/2016 | Keshavarz-Shokri et al. | |
| 2016/0228414 A1 | 8/2016 | Hadida Ruah et al. | |
| 2016/0229806 A1 | 8/2016 | Hurter et al. | |
| 2016/0237079 A1 | 8/2016 | Hadida Ruah et al. | |
| 2016/0271105 A1 | 9/2016 | Hadida Ruah et al. | |
| 2016/0303096 A1 | 10/2016 | Verwijs et al. | |
| 2016/0318931 A1 | 11/2016 | Hadida Ruah et al. | |
| 2016/0324788 A1 | 11/2016 | Hadida Ruah et al. | |
| 2016/0324846 A1 | 11/2016 | Verwijs et al. | |
| 2016/0332997 A1 | 11/2016 | Hadida Ruah et al. | |
| 2016/0354316 A1 | 12/2016 | Swinney et al. | |
| 2017/0087144 A1 | 3/2017 | Rowe et al. | |
| 2017/0100340 A1 | 4/2017 | Dokou et al. | |
| 2017/0107205 A1 | 4/2017 | Hadida Ruah et al. | |
| 2017/0107206 A1 | 4/2017 | Hadida Ruah et al. | |
| 2017/0189389 A1 | 7/2017 | Hadida-Ruah et al. | |
| 2017/0231970 A1 | 8/2017 | Hurter et al. | |
| 2017/0266176 A1 | 9/2017 | Alargova et al. | |
| 2018/0008546 A1 | 1/2018 | Verwijs et al. | |

FOREIGN PATENT DOCUMENTS

| | | |
|---|---|---|
| CA | 2 813 358 A1 | 10/2013 |
| CA | 2 813 472 A1 | 10/2013 |
| CA | 2 813 478 A1 | 10/2013 |
| CN | 1512987 A | 7/2004 |
| CN | 1898221 A | 1/2007 |
| CN | 101006076 A | 7/2007 |
| CN | 101151257 | 3/2008 |
| CN | 101287732 A | 10/2008 |
| CN | 101460489 | 6/2009 |
| CN | 101605543 A | 12/2009 |
| CN | 102731492 A | 10/2012 |
| CN | 104725628 A | 6/2015 |
| DE | 2735133 A1 | 2/1978 |
| DE | 102 51 019 A1 | 5/2004 |
| DE | 103 00 017 A1 | 7/2004 |
| DE | 10315377 A1 | 10/2004 |
| EA | 4925 B1 | 10/2004 |
| EA | 6155 B1 | 10/2005 |
| EP | 1380576 A | 3/1995 |
| EP | 1217000 A1 | 6/2002 |
| EP | 1864978 | 12/2007 |
| EP | 2264012 A1 | 12/2010 |
| FR | 2868417 A1 | 10/2005 |
| GB | 2525793 A | 11/2015 |
| JP | 61-103861 | 5/1986 |
| JP | 7-45466 B2 | 5/1995 |
| JP | 10213820 A | 8/1998 |
| JP | 2004-131393 A | 4/2004 |
| JP | 2006-282534 | 10/2006 |
| JP | 2009-530416 A | 8/2009 |
| JP | 2014-97964 A | 5/2014 |
| JP | 2014-232188 A | 12/2014 |
| JP | 2015-172005 A | 10/2015 |
| RU | 2005115965 A | 1/2006 |
| RU | 2005128828 A | 5/2006 |
| TW | I244393 B | 12/2005 |
| WO | WO 95/06046 | 3/1995 |
| WO | WO 96/19444 | 6/1996 |
| WO | WO 98/47868 | 10/1998 |
| WO | WO 98/58925 | 12/1998 |
| WO | WO 99/29318 | 6/1999 |
| WO | WO 00/16798 | 3/2000 |
| WO | WO 01/19822 A1 | 3/2001 |
| WO | WO 01/19830 A1 | 3/2001 |
| WO | WO 2001/19831 A1 | 3/2001 |
| WO | WO 01/23357 A2 | 4/2001 |
| WO | WO 01/53267 A1 | 7/2001 |
| WO | WO 2001/47916 A1 | 7/2001 |
| WO | WO 2002/16349 A1 | 2/2002 |
| WO | WO 0211883 | 2/2002 |
| WO | WO 0212236 | 2/2002 |
| WO | WO 02/032672 | 4/2002 |
| WO | WO 2002/059118 A1 | 8/2002 |
| WO | WO 03/002533 A1 | 1/2003 |
| WO | WO 03/007945 A1 | 1/2003 |
| WO | WO 2003/018536 A1 | 3/2003 |
| WO | WO 2003/041649 A2 | 5/2003 |
| WO | WO 03/055482 A1 | 7/2003 |
| WO | WO 03/093498 A1 | 11/2003 |
| WO | WO 2004/002481 A1 | 1/2004 |
| WO | WO 2004/007472 A1 | 1/2004 |
| WO | WO 2004/026873 A1 | 4/2004 |
| WO | WO 2004/028480 A2 | 4/2004 |
| WO | WO 2004/035571 A1 | 4/2004 |
| WO | WO 2004/037806 A1 | 5/2004 |
| WO | WO 2004/041277 A1 | 5/2004 |
| WO | WO 2004/041752 A2 | 5/2004 |
| WO | WO 2004/041788 A1 | 5/2004 |
| WO | WO 2004/056745 A2 | 7/2004 |
| WO | WO 2004/062601 A2 | 7/2004 |
| WO | WO 2004/072069 A1 | 8/2004 |
| WO | WO 2004/080972 A1 | 9/2004 |
| WO | WO 2004/087646 A2 | 10/2004 |
| WO | WO 2004/089470 A1 | 10/2004 |
| WO | WO 2004/091502 A2 | 10/2004 |
| WO | WO 2004/110352 A2 | 12/2004 |
| WO | WO 2004/111014 A1 | 12/2004 |
| WO | WO 2005/016884 A1 | 2/2005 |
| WO | WO 2005/026137 A2 | 3/2005 |
| WO | WO 2005/035514 A2 | 4/2005 |
| WO | WO 2005/037802 A1 | 4/2005 |

(56) References Cited

FOREIGN PATENT DOCUMENTS

| | | |
|---|---|---|
| WO | WO 2005/040135 A1 | 5/2005 |
| WO | WO 2005/049018 A1 | 6/2005 |
| WO | WO 2005/063746 A1 | 7/2005 |
| WO | WO 2005/075435 A1 | 8/2005 |
| WO | WO 2005/094374 A2 | 10/2005 |
| WO | WO 2005/120497 A2 | 12/2005 |
| WO | WO 2006/002421 A2 | 1/2006 |
| WO | WO 2006/010591 A2 | 2/2006 |
| WO | WO 2006/014012 A2 | 2/2006 |
| WO | WO 2006/034769 A1 | 4/2006 |
| WO | WO 2006/044456 A1 | 4/2006 |
| WO | WO 2006/044502 A2 | 4/2006 |
| WO | WO 2006/044503 A2 | 4/2006 |
| WO | WO 2006/044505 A2 | 4/2006 |
| WO | WO 2006/044682 A1 | 4/2006 |
| WO | WO 2006/045119 A2 | 4/2006 |
| WO | WO 2006/101740 A2 | 4/2006 |
| WO | WO 2006/057448 A1 | 6/2006 |
| WO | WO 2006/090817 A1 | 8/2006 |
| WO | WO 2006/100502 A1 | 9/2006 |
| WO | WO 2006/101740 | 9/2006 |
| WO | WO 2006099256 A2 | 9/2006 |
| WO | WO 2006/110483 A1 | 10/2006 |
| WO | WO 2006/113140 A2 | 10/2006 |
| WO | WO 2006/127588 A2 | 11/2006 |
| WO | WO 2007/021982 A2 | 2/2007 |
| WO | WO 2007/044560 A2 | 4/2007 |
| WO | WO 2007/056143 A2 | 5/2007 |
| WO | WO 2007/056341 A1 | 5/2007 |
| WO | WO 2007/065683 A1 | 6/2007 |
| WO | WO 2007/075567 A1 | 7/2007 |
| WO | WO 2007/075901 A2 | 7/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/106525 A1 | 9/2007 |
| WO | WO 2007/109605 A2 | 9/2007 |
| WO | WO 2007/111994 A2 | 10/2007 |
| WO | WO 2007117715 | 10/2007 |
| WO | WO 20074/146712 A2 | 12/2007 |
| WO | WO 2008/020227 A2 | 2/2008 |
| WO | WO 2008/029152 A2 | 3/2008 |
| WO | WO 2008/029168 A2 | 3/2008 |
| WO | WO 2008/051805 A2 | 5/2008 |
| WO | WO 2008/065732 A1 | 6/2008 |
| WO | WO 2008/127399 A2 | 10/2008 |
| WO | WO 2008/147952 A1 | 12/2008 |
| WO | WO 2008/156783 A2 | 12/2008 |
| WO | WO 2009/006315 A1 | 1/2009 |
| WO | WO 2009/012482 A2 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/055917 A1 | 5/2009 |
| WO | WO 2009/066775 A1 | 5/2009 |
| WO | WO 2009/073757 A1 | 6/2009 |
| WO | WO 2009/076141 A2 | 6/2009 |
| WO | WO 2009/076593 A1 | 6/2009 |
| WO | WO 2009/086426 A2 | 7/2009 |
| WO | WO 2009/127822 A2 | 10/2009 |
| WO | WO 2009/129501 A1 | 10/2009 |
| WO | WO 2009/138758 A2 | 11/2009 |
| WO | WO 2010/028159 A2 | 3/2010 |
| WO | WO 2010/028862 A1 | 3/2010 |
| WO | WO 2010/037066 A2 | 4/2010 |
| WO | WO 2010/048149 A2 | 4/2010 |
| WO | WO 2010/053471 A1 | 5/2010 |
| WO | WO 2010/054138 A2 | 5/2010 |
| WO | WO 2010/060952 A1 | 6/2010 |
| WO | WO 2010/065681 A1 | 6/2010 |
| WO | WO 2010/104307 A2 | 9/2010 |
| WO | WO 2010/112865 A1 | 10/2010 |
| WO | WO 2010/119264 A1 | 10/2010 |
| WO | WO 2010/137351 A1 | 12/2010 |
| WO | WO 2011/005355 A1 | 1/2011 |
| WO | WO 2011/029832 A1 | 3/2011 |
| WO | WO 2011/034506 A1 | 3/2011 |
| WO | WO 2011/050325 A1 | 4/2011 |
| WO | WO 2011/097300 A1 | 8/2011 |
| WO | WO 2011/109059 A1 | 9/2011 |
| WO | WO 2011/115892 A1 | 9/2011 |
| WO | WO 2011/119984 A1 | 9/2011 |
| WO | WO 2011/127290 A2 | 10/2011 |
| WO | WO 2011/133951 A1 | 10/2011 |
| WO | WO 2011/135549 A1 | 11/2011 |
| WO | WO 2011/146829 A1 | 11/2011 |
| WO | WO 2012/013282 A1 | 2/2012 |
| WO | WO 2012/016133 A2 | 2/2012 |
| WO | WO 2012/049555 A1 | 4/2012 |
| WO | WO 2012/052540 A1 | 4/2012 |
| WO | WO 2012/079583 A1 | 6/2012 |
| WO | WO 2012/116135 A2 | 8/2012 |
| WO | WO 2012/129562 A2 | 9/2012 |
| WO | WO 2013/005057 A1 | 1/2013 |
| WO | WO 2013/036869 A2 | 3/2013 |
| WO | WO 2013/038373 A1 | 3/2013 |
| WO | WO 2013/038378 A1 | 3/2013 |
| WO | WO 2013/038381 A1 | 3/2013 |
| WO | WO 2013/038390 A1 | 3/2013 |
| WO | WO 2013/045516 A1 | 4/2013 |
| WO | WO 2013/086131 A1 | 6/2013 |
| WO | WO 2013/092350 A1 | 6/2013 |
| WO | WO 2013/151739 A1 | 10/2013 |
| WO | WO 2013/179052 A1 | 12/2013 |
| WO | WO 2013/184198 A1 | 12/2013 |
| WO | WO 2013/185112 A1 | 12/2013 |
| WO | WO 2013/190212 A1 | 12/2013 |
| WO | WO 2014/002106 A1 | 1/2014 |
| WO | WO 2014/014841 A1 | 1/2014 |
| WO | WO 2014/047110 A2 | 3/2014 |
| WO | WO 2014/068893 A1 | 5/2014 |
| WO | WO 2014/078479 A2 | 5/2014 |
| WO | WO 2014/190199 A1 | 11/2014 |
| WO | WO 2015/036552 A1 | 3/2015 |
| WO | WO 2015/042297 A1 | 3/2015 |
| WO | WO 2015/054337 A1 | 4/2015 |
| WO | WO 2015/187905 A1 | 6/2015 |
| WO | WO 2015/134973 A1 | 9/2015 |
| WO | WO 2015/138909 A1 | 9/2015 |
| WO | WO 2015/138934 A1 | 9/2015 |
| WO | WO 2015/172046 A1 | 11/2015 |
| WO | WO 2015/173551 A1 | 11/2015 |
| WO | WO 2015/179414 A1 | 11/2015 |
| WO | WO 2015/196071 A1 | 12/2015 |
| WO | WO 2015/103317 A1 | 1/2016 |
| WO | WO 2016/025448 A2 | 2/2016 |
| WO | WO 2016/030524 A1 | 3/2016 |
| WO | WO 2016/040505 A1 | 3/2016 |
| WO | WO 2016/050208 A1 | 4/2016 |
| WO | WO 2016/050209 A1 | 4/2016 |
| WO | WO 2016/050210 A1 | 4/2016 |
| WO | WO 2016/057730 A1 | 4/2016 |
| WO | WO 2016/057811 A1 | 4/2016 |
| WO | WO 2016/062886 A1 | 4/2016 |
| WO | WO 2016/066582 A1 | 5/2016 |
| WO | WO 2016/086015 A1 | 6/2016 |
| WO | WO 2016/086103 A1 | 6/2016 |
| WO | WO 2016/086136 A1 | 6/2016 |
| WO | WO 2016/103176 A1 | 6/2016 |
| WO | WO 2016/105468 A1 | 6/2016 |
| WO | WO 2016/105477 A1 | 6/2016 |
| WO | WO 2016/105484 A1 | 6/2016 |
| WO | WO 2016/105485 A1 | 6/2016 |
| WO | WO 2016/107603 A1 | 7/2016 |
| WO | WO 2016/109362 A2 | 7/2016 |
| WO | WO 2016/115090 A1 | 7/2016 |
| WO | WO 2016/160945 A1 | 10/2016 |

OTHER PUBLICATIONS

Miyamatsu, et al., "A New Nonsteroidal Antiinflammatory Agent. 3.1 Analogs of 2-Substituted 5-Benzothiazoleacetic Acids and Their

(56) References Cited

OTHER PUBLICATIONS

Derivatives", Journal of Medicinal Chemistry (1974), vol. 17(5), pp. 491-496.
Stauffer, Shaun, R., et al., "Palladium-Catalyzed Arylation of Ethyl Cyanoacetate. Fluorescence Resonance Energy Transfer as a Tool for Reaction Discovery", Journal of the Americal Chemical Society, American Chemical Society, Washington, D.C.; US, vol. 123, No. 19 (Jan. 1, 2001), pp. 4641-4642.
Suzuki, Hitomi, et al., "A Simple One-Pot Conversion of Aryl Halides into Arylacetonitriles", The Chemical Society of Japan, Chemistry Letters, 1983, pp. 193-194.
PCT/US2011/033396 International Search Report, mailed Nov. 11, 2011.
International Preliminary Report on Patentability and Written Opinion of the International Search Authority for International Application No. PCT/US2011/033396, dated Oct. 23, 2012.
Notice of Allowance and Fee(s) Due for U.S. Appl. No. 14/286,708, dated Feb. 19, 2016.
Notice of Allowance and Fee(s) Due for U.S. Appl. No. 14/317,277, dated Feb. 24, 2016.
Notice of Allowance and Fee(s) Due for U.S. Appl. No. 14/334,902, dated Feb. 18, 2016.
Notice of Allowance and Fee(s) Due for U.S Appl. No. 14/532,791, dated Mar. 1, 2016.
Notice of Allowance and Fee(s) Due for U.S. Appl. No. 14/598,560, dated Jan. 21, 2016, Issue Fee paid Apr. 21, 2016.
Notice of Allowance and Fee(s) Due for U.S. Appl. No. 14/730,726, dated Apr. 12, 2016.
Notice of Allowance and Fee(s) Due for U.S. Appl. No. 14/341,163, dated Jan. 11, 2016, Issue Fee paid Apr. 8, 2016.
U.S. Appl. No. 13/091,411, filed Apr. 21, 2011.
U.S. Appl. No. 13/632,835, filed Oct. 1, 2012.
U.S. Appl. No. 14/077,885, filed Nov. 12, 2013.
U.S. Appl. No. 14/179,762, filed Feb. 13, 2014.
U.S. Appl. No. 14/444,451, filed Jul. 28, 2014.
U.S. Appl. No. 14/852,892, filed Sep. 14, 2015.
U.S. Appl. No. 14/870,592. filed Sep. 30, 2015.
U.S. Appl. No. 14/877,860, filed Oct. 7, 2015.
U.S. Appl. No. 14/920,836, filed Oct. 22, 2015.
U.S. Appl. No. 14/925,804, filed Oct. 28, 2015.
U.S. Appl. No. 14/935,777, filed Nov. 9, 2015.
U.S. Appl. No. 14/951,142, filed Nov. 24, 2015.
U.S. Appl. No. 14/982,973, filed Dec. 29, 2015.
U.S. Appl. No. 14/985,650, filed Dec. 31, 2015.
U.S. Appl. No. 14/992,132, filed Jan. 11, 2016.
U.S. Appl. No. 14/994,487, filed Jan. 13, 2016.
U.S. Appl. No. 14/996,781, filed Jan. 15, 2016.
U.S. Appl. No. 15/001,036. filed Jan. 19, 2016.
U.S. Appl. No. 15/043,049, filed Feb. 12, 2016.
U.S. Appl. No. 15/056,313, filed Feb. 29, 2016.
U.S. Appl. No. 15/056,436, filed Feb. 29, 2016.
U.S. Appl. No. 15/064,222, filed Mar. 8, 2016.
U.S. Appl. No. 15/073,591, filed Mar. 17, 2016.
U.S. Appl. No. 15/078,800. filed Mar. 23, 2016.
U.S. Appl. No. 15/093,582, filed Apr. 7, 2016.
Aridor et al., "Integration of endoplasmic reticulum signaling in health and disease," *Nature Med.*, 5(7): 745-751 (1999).
Bross et al., "Protein Misfolding and Degradation in Genetic Diseases," *Human Mut.*, 14: 186-198 (1999).
Cutting at al.. "A cluster of cystic fibrosis mutations in the first nucleotide-binding fold of the cystic fibrosis conductance regulator protein," *Nature*, 346: 366-369 (1990).
Dalemans et al., "Altered chloride ion channel kinetics associated with the ΔF508 cystic fibrosis mutation," *Nature*. 354: 526-528 (1991).
Database Registry, 1988, RN 117646-35-2. Retrieved from STN international [online]; retrieved on Feb. 13, 2015 (1 page).
Database Registry, 2004, RN 683220-08-8, Retrieved from STN international [online]; retrieved on Feb. 13, 2016.(1 page).

Dean et al., "Multiple mutations in highly conserved residues are found in mildly affected cystic fibrosis patients," *Cell*, 61: 863-870 (1990).
González et al., "Voltage Sensing by Fluorescence Resonance Energy Transfer in Single Cells,"0 *Biophys J*, 69(4): 1272-1280 (1995).
González et al, "Improved indicators of cell membrane potential that use fluorescence resonance energy transfer,"*Chem Biol*, 4(4): 269-277 (1997).
González, et al., "Cell-based assays and instrumentation for screening ion-channel targets, " *Drug Discov Today*, 4(9): 431-439 (1999).
Gregory et al., "Expression and characterization of the cystic fibrosis transmembrarie conductance regulator," *Nature*, 347: 382-386 (1990).
Kamal et al., "Ultrasonic activated efficient method for the cleavage of epoxides with aromatic amines," *Ultrasonics Sonochemistry*12(6):429-431 (2005).
Kerem et a, "Identification of the cystic fibrosis gene: genetic analysis," *Science*, 245: 1073-1080 (1989).
Kerem et al., "Identification of mutations in regions corresponding to the two putative nucleotide (ATP) binding folds of the cystic fibrosis gene," *Proc. Natl. Acad. Sci. USA*. 87: 8447-8451 (1990).
Morello et al., "Pharmacological chaperones: a new twist on receptor folding," *TiPS*, 21: 466-469 (2000).
Pasyk et al., "Mutant (ΔF506) cystic fibrosis transmembrane conductance regulator CT channel is functional when retained in endoplasmic reticulum of mammalian cells," *J. Biol Biochem*, 270(21): 12347-12350 (1995).
Quinton, "Cystic fibrosis a disease in electrolyte transport,"*FASEB J.*, 4: 2709-2717 (1990).
Rich et at. "Expression of cystic fibrosis transmembrane conductance regulator corrects defective chloride channel regulation in cystic fibrosis airway opithelial cells,"*Nature*, 347: 358-363 (1990).
Riordan et ai., "Identification of the cystic fibrosis gene: cloning and characterization of the complernentary DNA." *Science*245:1066-1073 (1989).
Ruteshauser et al., "Endoplasmic reticulum storage diseases," *Swiss Med Wkly*132: 211-222 (2002).
Shastry et al., "Neurodegenerative disorders of protein aggregation," *Neurochemistry International*, 43: 1-7 (2003).
English language abstract of CN 102731492 A, dated Oct. 17, 2012 (1 page).
English language abstract of DE 2735433 A1, dated Feb. 9, 1978 (1 page).
English language abstract of DE 10315377 A1, dated Oct. 14, 2004 (3 pages).
English language abstract of EP 2264012 A1, dated Dec. 22, 2012 (2 pages).
English language abstract of FR 2858417 A1, dated Oct. 7, 2005 (1 page).
English language abstract of JP 61103861 A, dated May 22, 1986 (4 pages).
English language abstract of JP 10213820, dated Aug. 11, 1998 (3 pages).
English language abstract of JP 2006282534, dated Oct. 19, 2006 (2 pages).
Bennett, J.C. and F. Plum (Eds.) (1996) *Cecil Textbook of Medicine*. 20th edition, vol. 2, pp. 1992-1996.
Bennett, J.C. and F. Plum (Eds.) (1996) *Cecil Textbook of Medicine*. 20th edition, vol. 2, pp. 2050-2057.
Berge, S.M. et al. (1977) "Pharmaceutical Salts" *J Pharm Sci*, 66(1):1-19.
Bjornsson, T.D. et al. (2003) "The conduct of in vitro and in vivo drug-drug interaction studies: A Pharmaceutical Research and Manufacturers of America (PhRMA) perspective" *Drug Metab Dispos*, 31(7):815-832.
Bombieri, C. et al. (1998) "Complete mutational screening of the CFTR gene in 120 patients with pulmonary disease" *Hum Genet*, 103:718-722.
Braun, J. et al. (1999) "No association between the deltaF508 cystic fibrosis mutation and type 2 diabetes mellitus" *Exp Clin Endocrinol*

(56) References Cited

OTHER PUBLICATIONS

*Diabetes*, 107(8):568-569. Abstract; PubMed PMID:10612489 [online]. Retrieved from http://www.ncbi.nlm.nih.gov/pubmed/10612489, on Sep. 24, 2012.
Brittain, H.G. (Ed.) *Polymorphism in Pharmaceutical Solids*. Marcel Dekker, 1999; p. 236.
Caira, M.R. (1998) "Crystalline Polymorphism of Organic Compounds" in *Topics of Current Chemistry*, 198:163-208.
Chen, R. et al. (2004) "Improved Dissolution of an Insoluble Drug Using a 4-Fluid Nozzle Spray-Drying Technique" *Chem Pharm Bull*, 52(9):1066-1070.
Chueshov, V.I. (Ed.) (2002) *Manufacturing Technologies of Drugs*. vol. 2. Kharkov:MTK-Kniga, Publishing House NPAU; excerpt, 7 pages.
Dahl, M. and B.G. Nordestgaard (2009) "Markers of early disease and prognosis in COPD" *Intl J COPD*, 4:157-167.
Dahl, M. et al. (Oct. 9, 2005) "Asthma and COPD in cystic fibrosis intron-8 5T carriers. A population-based study" *Respiratory Research*, 6:113, doi:10.1186/1465-9921-6-113, 9 pages.
European Patent Application No. 13167785.8, by Vertex Pharmaceuticals, Inc.: Extended European Search Report, including Opinion, dated Nov. 18, 2013.
European Patent Application No. 14172991.3, by Vertex Pharmaceuticals, Inc.: Extended European Search Report, including Opinion, dated Dec. 23, 2014.
European Patent Application No. 16154612.2, by Vertex Pharmaceuticals, Inc.: Extended European Search Report, including Opinion, dated Apr. 1, 2016.
European Patent Application No. 16155334.2, by Vertex Pharmaceuticals, Inc.: Extended European Search Report, including Opinion, dated Aug. 5, 2016.
Freireich, E.J. et al. (1966) "Quantitative comparison of toxicity of anticancer agents in mouse, rat, hamster, dog, monkey, and man" *Cancer Chemother Rep*, 50(4):219-244.
Fude, Cui (2002) *Pharmaceutics*. 1st Ed. China Medical Science Press, p. 443, 445-446. Chinese with English translation.
Fude, Cui (Feb. 2004) *Pharmaceutics*. 5th Ed. People's Medical Publishing House; p. 113-119, 334. Chinese with English translation.
Galietta, L.J.V. et al. (Jun. 1998) "An improved method to obtain highly differentiated monolayers of human bronchial epithelial cells" *In Vitro Cell Dev Biol*, 34:478-481.
Hancock, B. and M. Parks (2000) "What Is the True Solubility Advantage of Amorphous Pharmaceuticals?" *Pharm Res*, 17(4):397-404.
International Patent Application No. PCT/US2007/008975, filed Apr. 9, 2007, by Vertex Pharmaceuticals, Inc.: International Preliminary Report on Patentability and Written Opinion, dated Oct. 8, 2008.
International Patent Application No. PCT/US2007/008975, filed Apr. 9, 2007, by Vertex Pharmaceuticals, Inc.: International Search Report, dated Nov. 8, 2007.
International Patent Application No. PCT/US2008/012689, filed Nov. 12, 2008, by Vertex Pharmaceuticals, Inc.: International Preliminary Report on Patentability and Written Opinion, dated May 10, 2011.
International Patent Application No. PCT/US2008/012689, filed Nov. 12, 2008, by Vertex Pharmaceuticals, Inc.: International Search Report, dated Aug. 21, 2009.
International Patent Application No. PCT/US2009/063475, filed Nov. 6, 2009, by Vertex Pharmaceuticals, Inc.: International Search Report, dated Sep. 23, 2010.
International Patent Application No. PCT/US2009/063475, filed Nov. 6, 2009, by Vertex Pharmaceuticals, Inc.: International Preliminary Report on Patentability and Written Opinion, dated May 10, 2011.
International Patent Application No. PCT/US2011/030032, filed Mar. 25, 2011, by Vertex Pharmaceuticals, Inc.: International Search Report, dated Aug. 2, 2011.
International Patent Application No. PCT/US2011/030032, filed Mar. 25, 2011, by Vertex Pharmaceuticals, Inc.: International Preliminary Report on Patentability, dated Sep. 25, 2012.
International Patent Application No. PCT/US2011/033687, filed Apr. 22, 2011, by Vertex Pharmaceuticals, Inc.: International Search Report and Written Opinion, dated Aug. 30, 2011.
International Patent Application No. PCT/US2011/048565, filed Aug. 22, 2011, by Vertex Pharmaceuticals, Inc.: International Search Report and Written Opinion, dated Mar. 20, 2012.
International Patent Application No. PCT/US2011/051725, filed Sep. 15, 2011, by Vertex Pharmaceuticals, Inc.: International Search Report and Written Opinion, dated May 24, 2012.
International Patent Application No. PCT/US2012/064217, filed Nov. 8, 2012, by Vertex Pharmaceuticals, Inc.: International Search Report and Written Opinion, dated Jan. 15, 2013.
International Patent Application No. PCT/US2013/050557, filed Jul. 15, 2013, by Vertex Pharmaceuticals Inc.: International Search Report and Written Opinion, dated Sep. 30, 2013.
International Patent Application No. PCT/US2015/025722, filed Apr. 14, 2015, by Vertex Pharmaceuticals Inc.: International Search Report and Written Opinion, dated Jul. 3, 2015.
Ishiguro, H. et al. (2006) "Dysfunction of pancreatic $HCO_3$ secretion and pathogenesis of cystic fibrosis/chronic pancreatitis" *J Japan Pancreas Soc*, 21(1):13-25. Japanese with English abstract.
Jenkins, R. and R.L. Snyder (1996) *Introduction to X-Ray Powder Diffractometry*. New York, NY: John Wiley & Sons, Inc.; pp. 23-26.
Jones, A. and J.M. Helm (Jan. 1, 2009) "Emerging Treatments in Cystic Fibrosis" *Drugs*, 69(14):1903-1910.
Kawakami (Jan. 2010) "Formulation of a Poorly Water-soluble Drug by Decrystallization" Chapter 5 in *New Development of Property Evaluation and Formulation Design of Poorly Water Soluble Drugs*. CMC Publishing Co., Ltd.; pp. 212-244. Japanese with English abstract.
Kerem, E. et al. (2005) "Standards of care for patients with cystic fibrosis: a European consensus" *J Cystic Fibr*, 4:7-26.
Kerns, E.H. and L. Di (2008) *Drug-like Properties: Concepts, Structure Design and Methods: from ADME to Toxicity Optimization*. London, UK: Academic Press; pp. 122-136 and 197-208.
Konno, H. et al. (2008) "Effect of polymer type on the dissolution profile of amorphous solid dispersions containing felodipine" *Eur J Pharma Biopharma*, 70:493-499.
Krippendorff, B-F. et al. (2007) "Optimizing Classification of Drug-Drug Interaction Potential for CYP450 Isoenzyme Inhibition Assays in Early Drug Discovery" *J Biomol Screen*, 12(1):92-99.
Levin, M. and A.S. Verkman (Apr. 2005) "CFTR-Regulated Chloride Transport at the Ocular Surface in Living Mice Measured by Potential Differences" *Investigative Ophthalmology & Visual Science*, 46:1428-1434.
Notice of Allowance and Fee(s) Due for U.S. Appl. No. 13/871,349, dated Aug. 12, 2014.
Notice of Allowance and Fee(s) Due for U.S. Appl. No. 13/871,349, dated Apr. 17, 2015.
Notice of Allowance and Fee(s) Due for U.S. Appl. No. 13/871,349, dated Oct. 13, 2015.
Notice of Allowance and Fee(s) Due for U.S. Appl. No. 13/887,839, dated Jul. 7, 2014.
Notice of Allowance and Fee(s) Due for U.S. Appl. No. 13/887,839, dated Oct. 16, 2014.
Notice of Allowance and Fee(s) Due for U.S. Appl. No. 13/887,839, dated Feb. 2, 2015.
Notice of Allowance and Fee(s) Due for U.S. Appl. No. 13/887,839, dated Sep. 30, 2015.
Notice of Allowance and Fee(s) Due for U.S. Appl. No. 13/972,151, dated May 16, 2016.
Notice of Allowance and Fee(s) Due for U.S. Appl. No. 13/972,151, dated Sep. 8, 2016.
Notice of Allowance and Fee(s) Due for U.S. Appl. No. 14/031,360, dated Aug. 14, 2014.
Notice of Allowance and Fee(s) Due for U.S. Appl. No. 14/298,245, dated Jul. 21, 2015.
Notice of Allowance and Fee(s) Due for U.S. Appl. No. 14/298,245, dated Nov. 12, 2015.

(56) References Cited

OTHER PUBLICATIONS

Notice of Allowance and Fee(s) Due for U.S. Appl. No. 14/326,930, dated Dec. 8, 2015.
Notice of Allowance and Fee(s) Due for U.S. Appl. No. 14/326,930, dated Aug. 14, 2015.
Notice of Allowance and Fee(s) Due for U.S. Appl. No. 14/334,902, dated Oct. 19, 2015.
Notice of Allowance and Fee(s) Due for U.S. Appl. No. 14/532,791, dated Jul. 24, 2015.
Notice of Allowance and Fee(s) Due for U.S. Appl. No. 14/532,791, dated Nov. 6, 2015.
Notice of Allowance and Fee(s) Due for U.S. Appl. No. 14/567,475, dated Sep. 21, 2015.
Notice of Allowance and Fee(s) Due for U.S. Appl. No. 14/567,475, dated Jan. 5, 2016.
Notice of Allowance and Fee(s) Due for U.S. Appl. No. 14/579,098, dated Feb. 1, 2016.
Notice of Allowability for U.S. Appl. No. 14/579,098, dated Apr. 18, 2016.
Notice of Allowance and Fee(s) Due for U.S. Appl. No. 14/579,098, dated May 12, 2016.
Notice of Allowance and Fee(s) Due for U.S. Appl. No. 14/656,043, dated Aug. 4, 2016.
Notice of Allowance and Fee(s) Due for U.S. Appl. No. 14/687,286, dated Feb. 10, 2016.
Notice of Allowance and Fee(s) Due for U.S. Appl. No. 14/687,286, dated May 19, 2016.
Notice of Allowance and Fee(s) Due for U.S. Appl. No. 14/687,286, dated Sep. 28, 2016.
Notice of Allowance and Fee(s) Due for U.S. Appl. No. 14/877,914, dated Nov. 14, 2016.
Notice of Allowance and Fee(s) Due for U.S. Appl. No. 14/877,914, dated Jul. 27, 2016.
Notice of Allowance and Fee(s) Due for U.S. Appl. No. 14/925,804, dated May 17, 2016.
Notice of Allowance and Fee(s) Due for U.S. Appl. No. 15/073,591, dated Sep. 28, 2016.
Pettit, R.S. (2012) "Cystic Fibrosis Transmembrane Conductance Regulator—Modifying Medications: The Future of Cystic Fibrosis Treatment" *Annals of Pharmacotherapy*, 46:1065-1075.
Riley, R.J. et al. (2007) "Time-dependent CYP inhibition" *Expert Opin Drug Metab Toxicol*, 3:51-66.
Satoshi (2005) "Advances in male infertility therapy" *Urology View*, 3(6):58-61. Japanese with English abstract.
Stankovic, M. et al. (2008) "The CFTR M470V gene variant as a potential modifier of COPD severity: study of Serbian population" *Genetic Testing*, 12(3):357-362.
The Associated Press (Sep. 24, 2003) "FDA mulls drug to slow late-stage Alzheimer's" [online]. CNN.com. Retrieved from: http://www.cnn.com/2003/HEALTH/condtions/09/24/alzheimers.drug.ap/indexhtml, on Sep. 24, 2003.
The Free Online Dictionary, Definition of Amorphous [online]. Retrieved from: http://www.thefreedictionary.com/amorphous, on May 1, 2012.
Tzetis, M. et al. (2001) "CFTR gene mutations—including three novel nucleotide substitutions—and haplotype background in patients with asthma, disseminated bronchiectasis and chronic obstructive pulmonary disease" *Hum Genet*, 108:216-221.
U.S. Appl. No. 15/035,969, filed May 11, 2016, by Swinney et al.
U.S. Appl. No. 15/160,100, filed May 20, 2016, by DeMattei et al.
U.S. Appl. No. 15/170,263, filed Jun. 1, 2016, by Hadida-Ruah et al.
U.S. Appl. No. 15/173,325, filed Jun. 3, 2016, by Hadida-Ruah et al.
U.S. Appl. No. 15/181,114, filed Jun. 13, 2016, by Dokou et al.
U.S. Appl. No. 15/234,877, filed Aug. 11, 2016, by Hadida-Ruah et al.
U.S. Appl. No. 15/253,636, filed Aug. 31, 2016, by Rowe et al.
U.S. Appl. No. 15/297,983, filed Oct. 19, 2016, by Hadida Ruah et al.
U.S. Appl. No. 15/342,999, filed Nov. 3, 2016, by Alargova et al.
Van Goor, F. et al. (2006) "Rescue of deltaF508-CFTR trafficking and gating in human cystic fibrosis airway primary cultures by small molecules" *Am J Physiol Lung Cell Mol Physiol*, 290(6):L1117-L1130.
Vehring, R. (May 2008) "Pharmaceutical Particle Engineering via Spray Drying" *Pharm Res*, 25(5):999-1022.
Vertex Pharmaceuticals, Inc. (Apr. 5, 2012) "A phase 2, multicenter, double-blinded, placebo controlled, 3-part study to evaluate safety, efficacy, pharmacokinetics, and pharmacodynamics of VX-661 monotherapy and VX-661/VX-770 cotherapy in subjects with cystic fibrosis, homozygous for the F508del-CFTR mutation" [online]. Clinicaltrials.gov. Retrieved from: http://clinicaltrials.gov/archive/NCT01531673/2012 04-05; Identifier: NCT01531673.
Vertex Pharmaceuticals, Inc. (Apr. 18, 2013) "Treatment with VX-661 and Ivacaftor in a Phase 2 Study Resulted in Statistically Significant Improvements in Lung Function in People with Cystic Fibrosis Who Have Two Copies of the F508del Mutation" [online]. Cambridge, Mass.: *Business Wire*. Retrieved from: http://investors.vrtx.com/releasedetail.cfm?ReleaseID=757597.
Vertex Pharmaceuticals, Inc. (Jul. 18, 2013) "A Phase 2, Multi-center, Double-Blinded, Placebo Controlled, 3-Part Study to Evaluate Safety, Efficacy, Pharmacokinetics, and Pharmacodynamics of VX-661 Monotherapy and VX-661/VX-770 Cotherapy in Subjects With Cystic Fibrosis, Homozygous for the F508del-CFTR Mutation" [online]. ClinicalTrials.gov. Retrieved from: http://clinicaltrials.gov/archive/NCT01531673/2013 07 18; Identifier: NCT01531673.
Vertex Pharmaceuticals, Inc. (Mar. 25, 2014) "An Open-Label, Phase 1 Study in Healthy Adult Subjects to Examine the Effects of Multiple-Dose Ciprofloxacin on Ivacaftor and VX-661 in Combination With Ivacaftor" [online]. ClinicalTrials.gov. Retrieved from: https://clinicaltrials.gov/ct2/show/NCT02015507?term=vx-661&rank=4; Identifier: NCT02015507.
Vertex Pharmaceuticals, Inc. (May 1, 2014) "Addition of VX-661 to Kalydeco® (ivacaftor) Improves Lung Function in People with CF Who Are Heterozygous for the F508del and G551D Mutations in 28-day Phase 2 Proof-of-Concept Study" [online]. Boston: *Business Wire*. Retrieved from: http://investors.vrtx.com/releasedetail.cfm?ReleaseID=844677.
Vertex Pharmaceuticals, Inc. (Oct, 17, 2014) "Study to Evaluate Safety and Efficacy of VX-661 in Combination With Ivacaftor in Subjects With Cystic Fibrosis, Homozygous for the F508del-CFTR Mutation With an Open-Label Expansion" [online] ClinicalTrials.gov. Retrieved from: https://clinicaltrials.gov/ct2/show/NCT02070744?term=vx-661&rank=6; Identifier: NCT02070744.
Vertex Pharmaceuticals, Inc. (Mar. 23, 2015) "Vertex Announces Data from 12-Week Phase 2 Safety Study of VX-661 in Combination with Ivacaftor in People with Cystic Fibrosis Who Have Two Copies of the F508del Mutation" [online]. Boston: *Business Wire*. Retrieved from: http://investors.vrtx.com/releasedetail.cfm?ReleaseID=902790.
Vertex Pharmaceuticals, Inc. (May 5, 2015) "Study of VX-661 Alone and in Combination With Ivacaftor in Subjects Homozygous or Heterozygous to the F508del-Cystic Fibrosis Transmembrane Conductance Regulator (CFTR) Mutation" [online]. ClinicalTrials.gov, Identifier: NCT01531673. Retrieved from: https://clinicaltrials.gov/ct2/show/NCT01531673?term=vx-661&rank=3 (5 pages).
Wang, F. et al. (Mar. 1998) "Actions of genistein on cystic fibrosis transmembrane conductance regulator channel gating. Evidence for two binding sites with opposite effects" *J Gen Physiol*, 111(3):477-490.
Notice of Allowance and Fee(s) Due for U.S. Appl. No. 13/290,491, dated Oct. 25, 2012.
Notice of Allowance and Fee(s) Due for U.S. Appl. No. 15/001,036, dated Feb. 10, 2017.
Chiou, W.L. and S. Riegelman (Sep. 1971) "Pharmaceutical Applications of Solid Dispersion Systems" *J Pharm Sci*, 60(9):1281-1302.
Conti, S. et al. (2007) "Matrices containing NaCMC and HPMC 1. Dissolution performance characterization" *Intl J Pharma*, 333:136-142.

(56) References Cited

OTHER PUBLICATIONS

Friesen, D.T. et al. (2008) "Hydroxypropyl Methylcellulose Acetate Succinate-Based Spray-Dried Dispersions: An Overview" *Mol Pharma*, 5(6):1003-1019.

King, F.D. (Ed.) "Bioisosteres, Conformational Restriction and Pro-drugs—Case History: An Example of a Conformational Restriction Approach" in *Medical Chemistry: Principles and Practice*. 1994; Chapter 14, pp. 206-209.

Leuner, C. and J. Dressman (2000) "Improving drug solubility for oral delivery using solid dispersions" *Eur J Pharm Biopharm*, 50:47-60.

Notice of Allowance and Fee(s) Due for U.S. Appl. No. 14/027,791, dated Jul. 31, 2015.

Notice of Allowance and Fee(s) Due for U.S. Appl. No. 15/234,877, dated Jan. 11, 2018.

Notice of Allowance and Fee(s) Due for U.S. Appl. No. 15/584,324, dated Nov. 20, 2017.

Tanno, F. et al. (2004) "Evaluation of Hypromellose Acetate Succinate (HPMCAS) as a Carrier in Solid Dispersions" *Drug Dev Ind Pharm*, 30(1):9-17.

Vasiliou, V. et al. (Apr. 2009) "Human ATP-binding cassette (ABC) transporter family" *Hum Genomics*, 3(3):281-290.

Wallis, C. (2001) "Mucolytic therapy in cystic fibrosis" *J R Soc Med*, 94(Suppl 40):17-24.

Yu, H. et al. (2010) "VX-770, an investigational CFTR potentiator, acts on multiple CFTR forms in vitro" *Pediatric Pulmonology*, 45(33):318-319, Abstract 280.

Yu, H. et al. (2012) "Ivacaftor potentiation of multiple CFTR channels with gating mutations" *J Cystic Fibrosis*, 11(3):237-245.

Larock, R.C. and Yum, E.K. (1991) "Synthesis of Indoles via Palladium-Catalyzed Heteroannulation of Internal Alkynes," *J. Am. Chem. Soc.*, 113:6689-6690.

\* cited by examiner

PROCESS OF PRODUCING CYCLOALKYLCARBOXAMIDO-INDOLE COMPOUNDS

CROSS REFERENCE TO RELATED APPLICATIONS

This application is a divisional of U.S. utility patent application Ser. No. 13/642,642, filed Aug. 14, 2013, which is a United States National Phase filing of PCT Application No. PCT/US2011/33396, filed Apr. 21, 2011, which claims priority to U.S. provisional patent application Ser. Nos. 61/333,870, filed May 12, 2010; 61/329,510, filed Apr. 29, 2010; 61/329,500, filed Apr. 29, 2010; 61/329,493, filed Apr. 29, 2010; 61/327,099, filed Apr. 22, 2010; 61/327,095, filed Apr. 22, 2010; 61/327,091, filed Apr. 22, 2010; and 61/327,057, filed Apr. 22, 2010, the entire contents of all applications are incorporated herein by reference.

TECHNICAL FIELD OF THE INVENTION

The present invention features processes for preparing compounds useful for treating CFTR mediated diseases such as cystic fibrosis.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease. Other mutations include the R117H and G551D.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is disclosed in US published patent application US20090131492 (said publication being incorporated herein by reference in its entirety) as a modulator of CFTR activity and thus useful in treating CFTR-mediated diseases such as cystic fibrosis. There remains, however, a need for economical processes for the preparation of the cycloalkylcarboxamido-indole compounds described herein.

SUMMARY OF THE INVENTION

As described herein, the present invention provides processes for preparing CFTR correctors useful in the treatment of CFTR mediated diseases, such as cystic fibrosis. Such compounds include (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (hereinafter "Compound 1") which has the structure below:

Compound 1

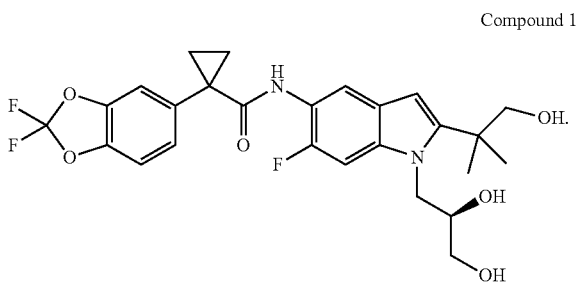 [SMILES: CC(C)(CO)c1cc2cc(NC(=O)C3(c4ccc5c(c4)OC(F)(F)O5)CC3)c(F)cc2n1C[C@@H](O)CO]

Compound 1 and pharmaceutically acceptable compositions thereof are useful for treating or lessening the severity of CFTR mediated diseases such as, for example, cystic fibrosis. Compound 1 may exist in several different solid forms such as substantially crystalline forms or amorphous forms.

DETAILED DESCRIPTION OF THE INVENTION

Definitions

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing, e.g. activity, by a measurable amount.

The term "chemically stable", as used herein, means that the solid form of Compound 1 does not decompose into one or more different chemical compounds when subjected to specified conditions, e.g., 40° C./75% relative humidity, for a specific period of time. e.g. 1 day, 2 days, 3 days, 1 week, 2 weeks, or longer. In some embodiments, less than 25% of the solid form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the solid form of Compound 1 decomposes.

The term "physically stable", as used herein, means that the solid form of Compound 1 does not change into one or more different physical forms of Compound 1 (e.g. different solid forms as measured by XRPD, DSC, etc.) when subjected to specific conditions, e.g., 40° C./75% relative humidity, for a specific period of time. e.g. 1 day, 2 days, 3 days, 1 week, 2 weeks, or longer. In some embodiments, less than 25% of the solid form of Compound 1 changes into one or more different physical forms when subjected to specified conditions. In some embodiments, less than about 20%, less than about 15%, less than about 10%, less than about 5%, less than about 3%, less than about 1%, less than about 0.5% of the solid form of Compound 1 changes into one or more different physical forms of Compound 1 when subjected to specified conditions. In some embodiments, no detectable amount of the solid form of Compound 1 changes into one or more physically different solid forms of Compound 1.

As used herein, the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. All tautomeric forms of the Compound 1 are included herein. For example, Compound 1 may exist as tautomers, both of which are included herein:

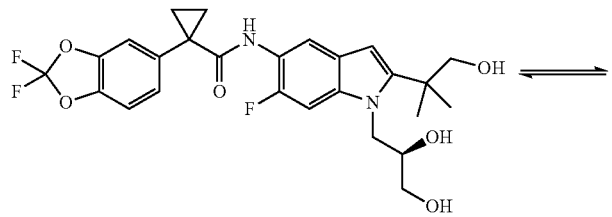 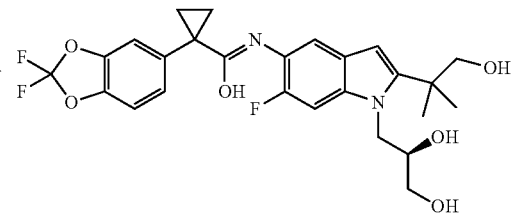

Additionally, unless otherwise stated, structures depicted herein are also meant to include compounds that differ only in the presence of one or more isotopically enriched atoms. For example, Compound 1, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or compounds with improved therapeutic profile.

The term "protecting group," abbreviated as P, as used herein refers to any chemical group introduced into a molecule by chemical modification of a functional group in order to obtain chemoselectivity in a subsequent chemical reaction. Non-limiting examples of alcohol protecting groups include acetyl (Ac), benzoyl (Bz), benzyl (Bn), β-methoxyethoxymethyl ether (MEM), dimethoxytrityl (DMT), methoxymethyl ether (MOM), methoxytrityl (MMT), p-methoxybenzyl ether (PMB), pivaloyl (Piv), tetrahydropyranyl (THP), trityl (Tr), and trimethylsilyl (TMS). In one embodiment, the protecting group is Bn which has the structure —CH$_2$C$_6$H$_5$.

The abbreviation "DCM" stands for dichloromethane. The abbreviation "IPA" stands for isopropyl alcohol. The abbreviation "DMSO" stands for dimethylsulfoxide. The abbreviation "MTBE" stands for methyl t-butyl ether. The abbreviation "THF" stands for tetrahydrofuran. The abbreviation "TEA" stands for triethylamine. The abbreviation "dba" as in Pd(dba)$_2$ stands for dibenzylideneacetone. The abbreviation "dppf" as in Pd(dppf)Cl$_2$ stands for stands for 1,1'-bis(diphenylphosphino) ferrocene.

In one aspect, the invention features a method for preparing a compound of formula I:

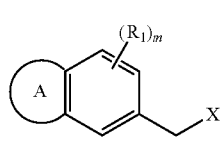

I wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
X is CN or CO$_2$R;
R is C$_{1-6}$ aliphatic or aryl; and
m is an integer from 0 to 3 inclusive;

comprising the steps of
a) reacting a compound of formula IA in a first organic solvent

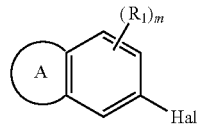

IA wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
m is an integer from 0 to 3 inclusive; and
Hal is a halide;
with a compound of formula IB:

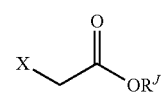

IB wherein R$^J$ is hydrogen or C$_{1-6}$ aliphatic, to form a compound of formula IC:

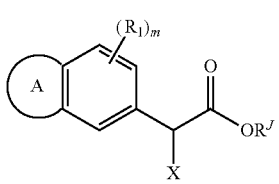

IC wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
X is CN or CO$_2$R;
R is R is C$_{1-6}$ aliphatic or aryl; and
m is an integer from 0 to 3 inclusive; and b) removing the —CO$_2$R$^J$ group from compound IC in a second organic solvent to form a compound of formula I.

In another embodiment, the invention features the above method wherein ring A is a fused heterocycloalkyl or heteroaryl. In another embodiment, ring A is selected from

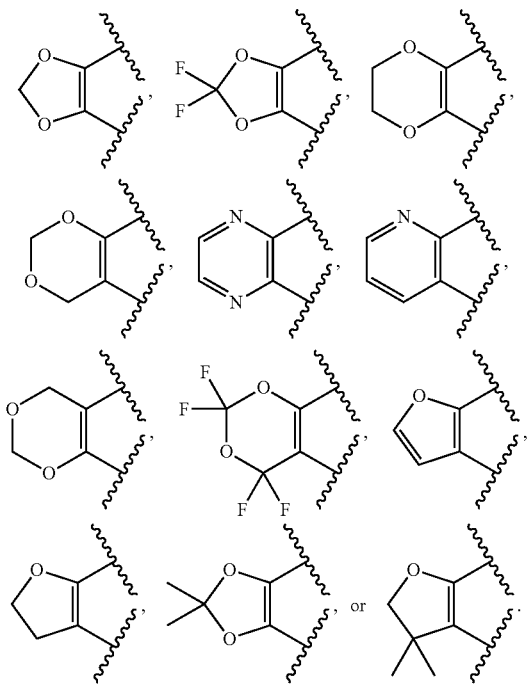

In another embodiment, ring A is

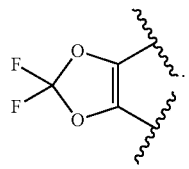 [SMILES: *C1=C(*)OC(F)(F)O1]

In another embodiment, the invention features the above method wherein X is CN. In another embodiment, X is CO$_2$Et.

In another embodiment, the invention features the above method wherein m is 0.

In another embodiment, the invention features the above method wherein R$^J$ is a C$_{1-6}$ aliphatic. In another embodiment, R$^J$ is —CH$_2$CH$_3$.

In another embodiment, the invention features the above method wherein Hal is Br.

In another embodiment, the invention features the above method wherein the first organic solvent is an aprotic solvent. In another embodiment, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the first organic solvent is selected from acetonitrile, toluene, benzene, or xylenes. In another embodiment, the first organic solvent is toluene.

In another embodiment, the invention features the above method wherein step a) is carried out in the presence of a transition metal catalyst. In another embodiment, step a) is carried out in the presence of a palladium catalyst. In another embodiment, step a) is carried out in the presence of a palladium catalyst selected from palladium(II)acetate, Pd(dppf)Cl$_2$, Pd(dba)$_2$, tetrakis(triphenylphosphine)palladium(0) or tris(dibenzylideneacetone)dipalladium(0). In another embodiment, step a) is carried out in the presence of Pd(dba)$_2$.

In another embodiment, the invention features the above method wherein step a) is carried out at about 50° C. to 90° C. In another embodiment, step a) is carried out at about 60° C. to 80° C. In another embodiment, step a) is carried out at about 70° C.

In another embodiment, the invention features the above method wherein the second organic solvent is an aprotic solvent. In another embodiment, the second organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the second organic solvent is dimethylsulfoxide.

In another embodiment, the invention features the above method wherein step b) is carried out in the presence of an inorganic acid. In another embodiment, step b) is carried out in the presence of an inorganic acid selected from hydrochloric, sulfuric, nitric, phosphoric, or boric acid. In another embodiment, step b) is carried out in the presence of hydrochloric acid.

In another embodiment, the invention features the above method wherein step b) is carried out at about 55° C. to 95° C. In another embodiment, step b) is carried out at about 65° C. to 85° C. In another embodiment, step b) is carried out at about 75° C.

In another aspect, the invention features a method for preparing a compound of formula II:

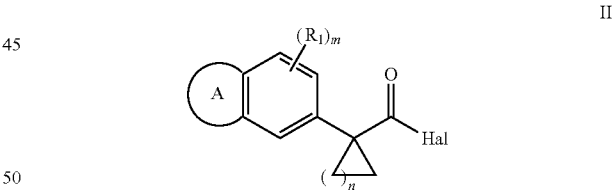

wherein, independently for each occurrence:
ring A is a fused cycloalkyl, heterocycloalkyl, aryl, or heteroaryl ring;
Hal is a halide;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
m is an integer from 0 to 3 inclusive; and
n is an integer from 1 to 4 inclusive;
comprising the steps of
a) reacting a compound of formula IIA in a first organic solvent

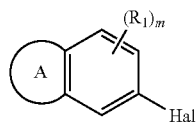

wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
m is an integer from 0 to 3 inclusive; and
Hal is a halide;
with a compound of formula IIB:

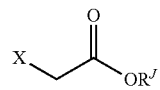

wherein
X is CN or CO$_2$R;
R is C$_{1-6}$ aliphatic or aryl; and
R$^J$ is hydrogen or C$_{1-6}$ aliphatic, to form a compound of formula IIC:

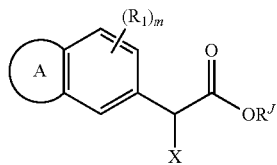

wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
X is CN or CO$_2$R;
R is C$_{1-6}$ aliphatic or aryl; and
m is an integer from 0 to 3 inclusive;
b) removing the —CO$_2$R$^J$ group from compound IIC in a second organic solvent to form a compound of formula I:

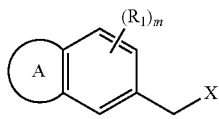

wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
X is CN or CO$_2$R;
R is C$_{1-6}$ aliphatic or aryl; and
m is an integer from 0 to 3 inclusive;
c) reacting a compound of formula I with a compound of formula IID in the presence of a base:

wherein, independently for each occurrence:
Hal is a halide; and
q is an integer from 0 to 3 inclusive; to produce a compound of formula IIE:

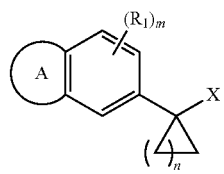

wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
m is an integer from 0 to 3 inclusive;
X is CN or CO$_2$R;
R is C$_{1-6}$ aliphatic or aryl; and
n is an integer from 1 to 4 inclusive;
d) sequentially reacting a compound of formula IIE with a hydroxide base and acid to form a compound of formula IIF:

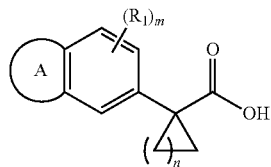

wherein, independently for each occurrence:
ring A is a fused cycloalkyl, heterocycloalkyl, aryl, or heteroaryl ring;
R$_1$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

m is an integer from 0 to 3 inclusive; and n is an integer from 1 to 4 inclusive; and e) reacting a compound of formula IIF with a halogenating agent in a third organic solvent to form a compound of formula II.

In another embodiment, the invention features the above method wherein in step a), the first organic solvent is an aprotic solvent. In another embodiment, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the first organic solvent is toluene.

In another embodiment, the invention features the above method wherein in step a), m is 0.

In another embodiment, the invention features the above method wherein in step a), Hal is Br.

In another embodiment, the invention features the above method wherein in step a), ring A is a fused heterocyclic or heteroaryl ring. In another embodiment, ring A is selected from

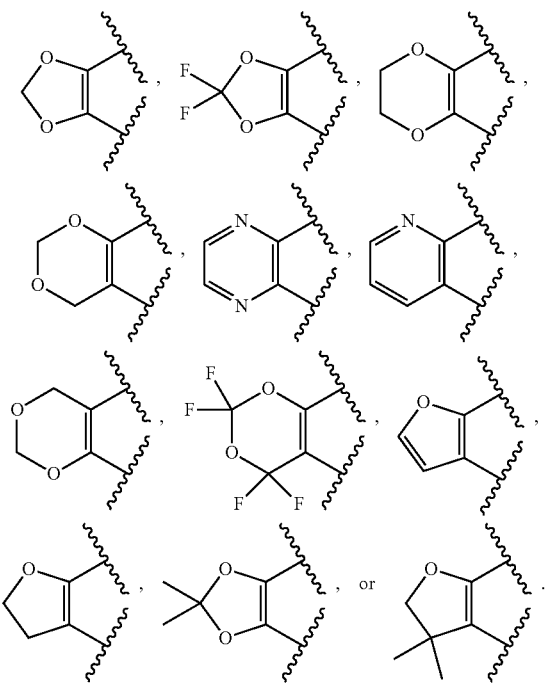

In another embodiment, ring A is

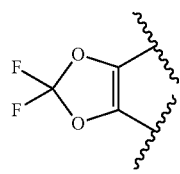

In another embodiment, the invention features the above method wherein in step a), X is CN. In another embodiment, X is CO$_2$Et.

In another embodiment, the invention features the above method wherein in step a) R$^J$ is Et.

In another embodiment, the invention features the above method wherein in formula IIC, ring A is

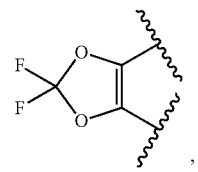 [SMILES: *C1=C(*)OC(F)(F)O1]

m is 0, X is CN, and R$^J$ is Et.

In another embodiment, the invention features the above method wherein in step b), the second solvent is an aprotic solvent. In another embodiment, the second solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the second solvent is dimethylsulfoxide.

In another embodiment, the invention features the above method wherein in formula I, ring A is

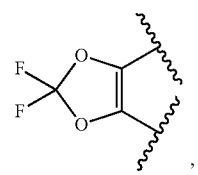 [SMILES: *C1=C(*)OC(F)(F)O1]

m is 0, and X is CN.

In another embodiment, the invention features the above method wherein in step c), the base is an inorganic base. In another embodiment, the base is a hydroxide. In another embodiment, the base is NaOH.

In another embodiment, the invention features the above method wherein in formula IID, q is 1.

In another embodiment, the invention features the above method wherein in formula IID, one Hal is Cl and the other Hal is Br.

In another embodiment, the invention features the above method wherein in step d), the base is NaOH. In another embodiment, in step d), the acid is HCl.

In another embodiment, the invention features the above method wherein in step d), reaction with a hydroxide base takes place at about 60° C. to 100° C. In another embodiment, reaction with a hydroxide takes place at about 70° C. to 90° C. In another embodiment, reaction with a hydroxide takes place at about 80° C.

In another embodiment, the invention features the above method wherein in formula IIE, ring A is

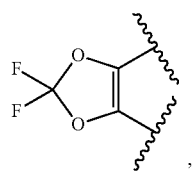

m is 0, n is 1, and X is CN.

In another embodiment, the invention features the above method wherein in step e), the third organic solvent is an aprotic solvent. In another embodiment, in step e), the third organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step e), the third organic solvent is toluene.

In another embodiment, the invention features the above method wherein in step e), the halogenating agent is $SOCl_2$.

In another embodiment, the invention features the above method wherein step e) takes place at about 40° C. to 80° C. In another embodiment, step e) takes place at about 50° C. to 70° C. In another embodiment, step e) takes place at about 60° C.

In another embodiment, the invention features the above method wherein in formula IIF, ring A is

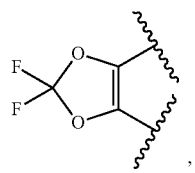

m is 0, and n is 1.

In another embodiment, the invention features the above method wherein in formula II, ring A is

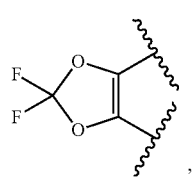

m is 0, n is 1, and Hal is Cl.

In another aspect, the invention features a method of preparing a compound of formula III:

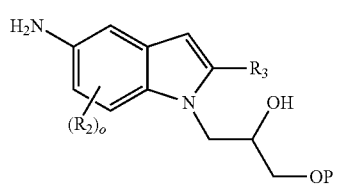

III wherein, independently for each occurrence:

$R_2$ is $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;

$R^J$ is hydrogen or $C_{1-6}$ aliphatic;

$R_3$ is $C_{1-6}$ aliphatic optionally substituted with OH, OP, $-O-C_{1-6}$ aliphatic, aryl, heteroaryl, $-O$-aryl, or $-O$-heteroaryl;

P is a protecting group; and o is an integer from 0 to 3;

comprising the steps of:

a) reacting a compound of formula IIIA:

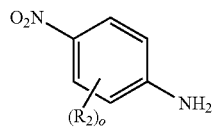

IIIA wherein, independently for each occurrence:

$R_2$ is $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;

$R^J$ is hydrogen or $C_{1-6}$ aliphatic; and o is an integer from 0 to 3;

with a halogenating reagent in a first organic solvent to form a compound of formula IIIB:

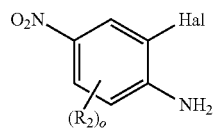

IIIB wherein, independently for each occurrence:

$R_2$ is $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;

$R^J$ is hydrogen or $C_{1-6}$ aliphatic;

o is an integer from 0 to 3; and

Hal is a halide;

b) reacting the compound of formula IIIB in a second organic solvent with a compound of formula IIIC:

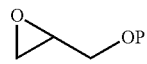

IIIC wherein:

P is a protecting group;

followed by reduction and treatment with acid to form a compound of formula IIID:

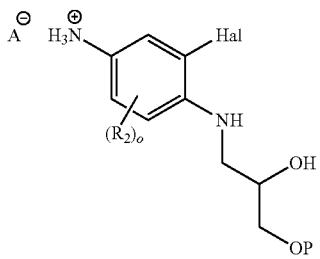

wherein:
$R_2$ is $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
$R^J$ is hydrogen or $C_{1-6}$ aliphatic;
o is an integer from 0 to 3;
Hal is a halide;
P is a protecting group; and
$A^\ominus$ is an anion;

c) neutralizing a compound of formula IIID in the presence of a base to form a compound of formula IIID-a:

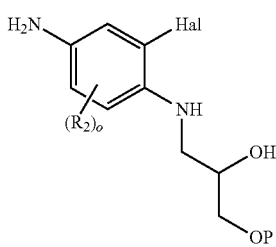

wherein:
$R_2$ is $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
$R^J$ is hydrogen or $C_{1-6}$ aliphatic;
o is an integer from 0 to 3;
Hal is a halide; and
P is a protecting group;

d) reacting a compound of formula IIID-a in a third organic solvent with a compound of formula IIIE:

wherein, independently for each occurrence:
$R_3$ is a $C_{1-6}$ aliphatic optionally substituted with OH, OP, $-O-C_{1-6}$ aliphatic, aryl, heteroaryl, $-O$-aryl, or $-O$-heteroaryl;
in the presence of a catalyst to form a compound of formula III.

In another embodiment, the invention features the above method wherein in formula IIIA, o is 1. In another embodiment, o is 1 and $R_2$ is F.

In another embodiment, the invention features the above method wherein in step a), the halogenating reagent is N-bromosuccinimide.

In another embodiment, the invention features the above method wherein in step a), the first organic solvent is an aprotic solvent. In another embodiment, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the first organic solvent is ethyl acetate.

In another embodiment, the invention features the above method wherein step a) takes place at about 2° C. to 42° C. In another embodiment, step a) takes place at about 12° C. to 32° C. In another embodiment, step a) takes place at about 22° C.

In another embodiment, the invention features the above method wherein in formula IIIB, o is 1, $R_2$ is F, and Hal is Br.

In another embodiment, the invention features the above method wherein in formula IIIC, P is benzyl.

In another embodiment, the invention features the above method wherein in step b), the second organic solvent is an aprotic solvent. In another embodiment, in step b), the second organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step b), the second organic solvent is toluene.

In another embodiment, the invention features the above method wherein in step b), the reaction with a compound of formula IIIC takes place at about 60° C. to 100° C. In another embodiment, in step b), the reaction with a compound of formula IIIC takes place at about 70° C. to 90° C. In another embodiment, in step b), the reaction with a compound of formula IIIC takes place at about 80° C.

In another embodiment, the invention features the above method wherein in step b), reduction is carried out with hydrogen.

In another embodiment, the invention features the above method wherein in step b), the acid is p-toluenesulfonic acid.

In another embodiment, the invention features the above method wherein in formula IIID, o is 1, $R_2$ is F, Hal is Br, $A^-$ is $Tos^-$, and P is benzyl.

In another embodiment, the invention features the above method wherein in formula IIIE, $R_3$ is $C(CH_3)_2CH_2O$(benzyl).

In another embodiment, the invention features the above method wherein in step c), the base is an inorganic base.

In another embodiment, the invention features the above method wherein in step c), the base is $NaHCO_3$.

In another embodiment, the invention features the above method wherein in step d), the third organic solvent is an aprotic solvent. In another embodiment, in step d), the third organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step d), the third organic solvent is acetonitrile.

In another embodiment, the invention features the above method wherein step d) takes place at about 60° C. to 100°

C. In another embodiment, step d) takes place at about 70° C. to 90° C. In another embodiment, step d) takes place at about 80° C.

In another embodiment, the invention features the above method wherein in step d), the catalyst is a palladium catalyst. In another embodiment, in step d), the catalyst is selected from palladium(II)acetate, Pd(dppf)Cl$_2$, Pd(dba)$_2$, (MeCN)$_2$PdCl$_2$, tetrakis(triphenylphosphine)palladium(0) or tris(dibenzylideneacetone)dipalladium(0). In another embodiment, in step d), the catalyst is palladium(II)acetate.

In another aspect, the invention features a method of preparing a compound of formula IV:

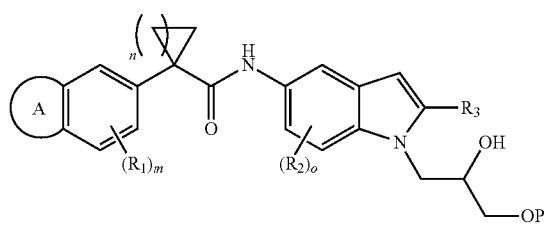

IV wherein, independently for each occurrence:

ring A is a fused cycloalkyl, heterocycloalkyl, aryl, or heteroaryl ring;

R$_1$ and R$_2$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

R$_3$ is a C$_{1-6}$ aliphatic optionally substituted with OH, OP, —O—C$_{1-6}$ aliphatic, aryl, heteroaryl, —O-aryl, or —O-heteroaryl;

P is a protecting group;

m is an integer from 0 to 3 inclusive;

n is an integer from 1 to 4 inclusive; and o is an integer from 1 to 3 inclusive;

comprising the steps of:

a) reacting a compound of formula IIIA:

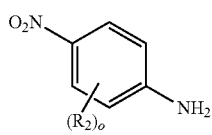

IIIA wherein, independently for each occurrence:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic; and o is an integer from 0 to 3;

with a halogenating reagent in a first organic solvent to form a compound of formula IIIB:

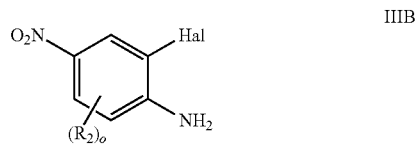

IIIB wherein, independently for each occurrence:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

o is an integer from 0 to 3; and

Hal is a halide;

b) reacting the compound of formula IIIB in a second organic solvent with a compound of formula IIIC:

IIIC wherein:

P is a protecting group;

followed by reduction and treatment with acid to form a compound of formula IIID:

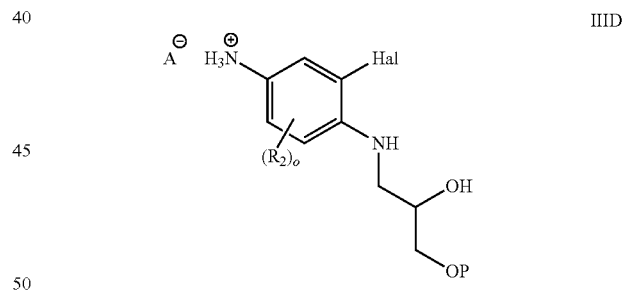

IIID wherein:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

o is an integer from 0 to 3;

Hal is a halide;

P is a protecting group; and

A$^\ominus$ is an anion;

c) neutralizing a compound of formula IIID in the presence of a base to form a compound of formula IIID-a:

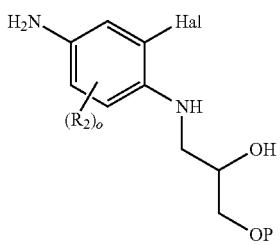

IIID-a wherein:

R₂ is —R$^J$, —OR$^J$, —N(R$^J$)₂, —NO₂, halogen, —CN, —C$_{1-4}$haloalkyl, —C$_{1-4}$haloalkoxy, —C(O)N(R$^J$)₂, —NR$^J$C(O)R$^J$, —SOR$^J$, —SO₂R$^J$, —SO₂N(R$^J$)₂, —NR$^J$SO₂R$^J$, —COR$^J$, —CO₂R$^J$, —NR$^J$SO₂N(R$^J$)₂, —COCOR$^J$;

R$^J$ is hydrogen or C$_{1-6}$ aliphatic;

o is an integer from 0 to 3;

Hal is a halide; and

P is a protecting group;

d) reacting a compound of formula IIID in a third organic solvent with a compound of formula IIIE:

IIIE wherein, independently for each occurrence:

R₃ is a C$_{1-6}$ aliphatic optionally substituted with OH, OP, —O—C$_{1-6}$ aliphatic, aryl, heteroaryl, —O-aryl, or —O-heteroaryl;

in the presence of a catalyst to form a compound of formula III:

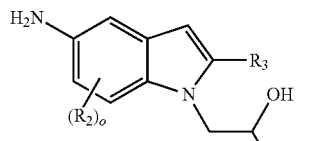

III wherein, independently for each occurrence:

R₂ is —R$^J$, —OR$^J$, —N(R$^J$)₂, —NO₂, halogen, —CN, —C$_{1-4}$haloalkyl, —C$_{1-4}$haloalkoxy, —C(O)N(R$^J$)₂, —NR$^J$C(O)R$^J$, —SOR$^J$, —SO₂R$^J$, —SO₂N(R$^J$)₂, —NR$^J$SO₂R$^J$, —COR$^J$, —CO₂R$^J$, —NR$^J$SO₂N(R$^J$)₂, —COCOR$^J$;

R$^J$ is hydrogen or C$_{1-6}$ aliphatic;

R₃ is C$_{1-6}$ aliphatic optionally substituted with OH, OP, —O—C$_{1-6}$ aliphatic, aryl, heteroaryl, —O-aryl, or —O-heteroaryl;

P is a protecting group; and o is an integer from 0 to 3;

e) reacting the compound of formula III in a fourth organic solvent with a compound of formula II:

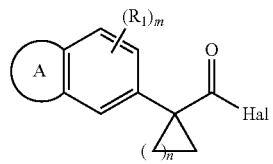

II wherein, independently for each occurrence:

ring A is a fused cycloalkyl, heterocycloalkyl, aryl, or heteroaryl ring;

Hal is a halide;

R₁ is independently selected from —R$^J$, —OR$^J$, —N(R$^J$)₂, —NO₂, halogen, —CN, —C$_{1-4}$haloalkyl, —C$_{1-4}$haloalkoxy, —C(O)N(R$^J$)₂, —NR$^J$C(O)R$^J$, —SOR$^J$, —SO₂R$^J$, —SO₂N(R$^J$)₂, —NR$^J$SO₂R$^J$, —COR$^J$, —CO₂R$^J$, —NR$^J$SO₂N(R$^J$)₂, —COCOR$^J$;

R$^J$ is hydrogen or C$_{1-6}$ aliphatic;

m is an integer from 0 to 3 inclusive; and n is an integer from 1 to 4 inclusive;

to form the compound of formula IV.

In another embodiment, the invention features the above method wherein in formula IV, ring A is selected from

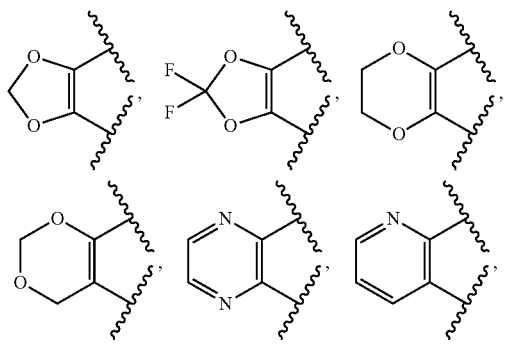

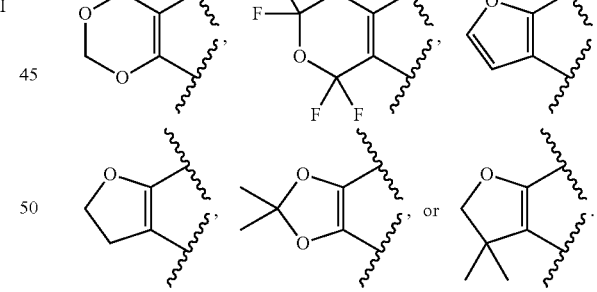

, or

In another embodiment, in formula IV, ring A is

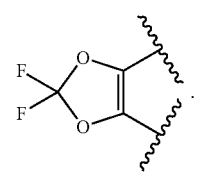

.

In another embodiment, the invention features the above method wherein in formula IV, m is 0. In another embodiment, in formula IV, n is 1. In another embodiment, in formula IV, o is 1 and $R_2$ is F.

In another embodiment, the invention features the above method wherein in formula IV, P is benzyl.

In another embodiment, the invention features the above method wherein in formula IV, $R_3$ is a $C_4$ aliphatic optionally substituted with OP. In another embodiment, in formula IV, $R_3$ is

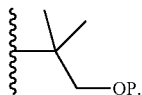

In another embodiment, in formula IV, $R_3$ is

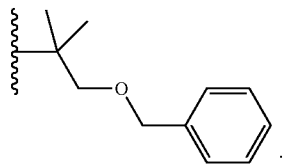 [SMILES: *C(C)(C)COCc1ccccc1]

In another embodiment, the invention features the above method wherein in formula IV, ring A is

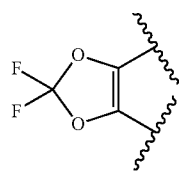

m is 0, n is 1, o is 1 and $R_2$ is F, P is benzyl, and $R_3$ is

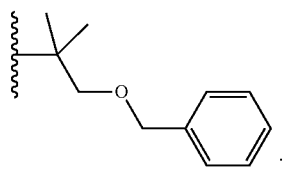 [SMILES: *C(C)(C)COCc1ccccc1]

In another embodiment, the invention features the above method wherein in step a), the halogenating reagent is N-bromosuccinimide.

In another embodiment, the invention features the above method wherein in step a), the first organic solvent is an aprotic solvent. In another embodiment, in step a), the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step a), the first organic solvent is ethyl acetate.

In another embodiment, the invention features the above method wherein step a) takes place at about 2° C. to 42° C. In another embodiment, step a) takes place at about 12° C. to 32° C. In another embodiment, step a) takes place at about 22° C.

In another embodiment, the invention features the above method wherein in formula IIIB, o is 1, $R_2$ is F, and Hal is Br.

In another embodiment, the invention features the above method wherein in formula IIIC, P is benzyl.

In another embodiment, the invention features the above method wherein in step b), the second organic solvent is an aprotic solvent. In another embodiment, in step b), the second organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step b), the second organic solvent is toluene.

In another embodiment, the invention features the above method wherein in step b), the reaction with a compound of formula IIIC takes place at about 60° C. to 100° C. In another embodiment, in step b), the reaction with a compound of formula IIIC takes place at about 70° C. to 90° C. In another embodiment, in step b), the reaction with a compound of formula IIIC takes place at about 80° C.

In another embodiment, the invention features the above method wherein in step b), reduction is carried out with hydrogen.

In another embodiment, the invention features the above method wherein in step b), the acid is p-toluenesulfonic acid.

In another embodiment, the invention features the above method wherein in formula IIID, o is 1, $R_2$ is F, Hal is Br, $A^-$ is Tos$^-$, and P is benzyl.

In another embodiment, the invention features the above method wherein in formula IIIE, $R_3$ is $C(CH_3)_2CH_2O$(benzyl).

In another embodiment, the invention features the above method wherein in step c), the base is an inorganic base.

In another embodiment, the invention features the above method wherein in step c), the base is $NaHCO_3$.

In another embodiment, the invention features the above method wherein in step d), the third organic solvent is an aprotic solvent. In another embodiment, in step d), the third organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step d), the third organic solvent is acetonitrile.

In another embodiment, the invention features the above method wherein step d) takes place at about 60° C. to 100° C. In another embodiment, step d) takes place at about 70° C. to 90° C. In another embodiment, step d) takes place at about 80° C.

In another embodiment, the invention features the above method wherein in step d), the catalyst is a palladium catalyst. In another embodiment, in step d), the catalyst is selected from palladium(II)acetate, Pd(dppf)Cl$_2$, Pd(dba)$_2$, tetrakis(triphenylphosphine)palladium(0) or tris(dibenzylideneacetone)dipalladium(0). In another embodiment, in step d), the catalyst is palladium(II)acetate.

In another embodiment, the invention features the above method wherein in step e), ring A is

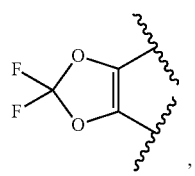

m is 0, n is 1, and Hal is Cl.

In another embodiment, the invention features the above method wherein in step e), the fourth organic solvent is an aprotic solvent. In another embodiment, in step e), the fourth organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step e), the fourth organic solvent is dichloromethane.

In another embodiment, the invention features the above method wherein step e) takes place at about −20° C. to 20° C. In another embodiment, step e) takes place at about −10° C. to 10° C. In another embodiment, step e) takes place at about 0° C.

In another embodiment, the invention features the above method wherein in step e), the compound of formula II is prepared in situ by halogenating the acid precursor and reacted with the compound of formula III without isolation.

In another embodiment, the invention features the above method further comprising removing the two protecting groups from the compound of formula IV to form a compound of formula IVA:

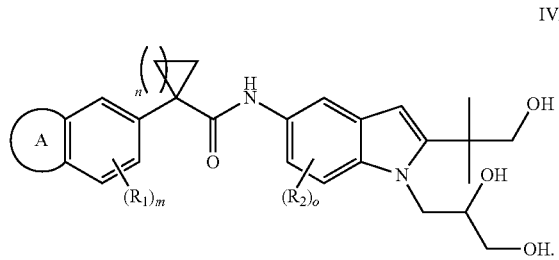

IVA

In another embodiment, the protecting groups are removed by hydrogenation.

In another aspect, the invention features a method of preparing Compound 1:

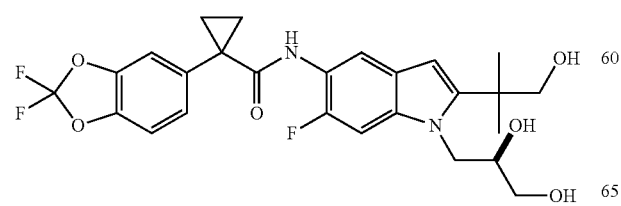

1 comprising the steps of:
a) reacting compound 2:

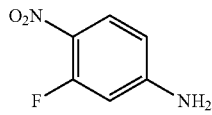

2 with a brominating reagent to form a compound 3:

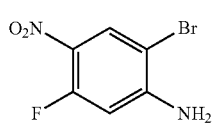

3 b) reacting compound 3 with compound 4:

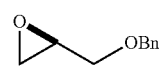

4 followed by reduction to form compound 5:

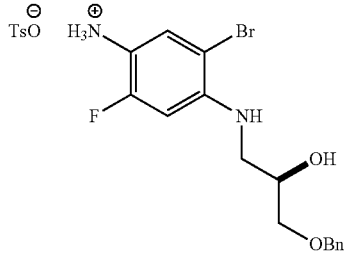

5 followed by neutralizing compound 5 with a base to give compound 5a:

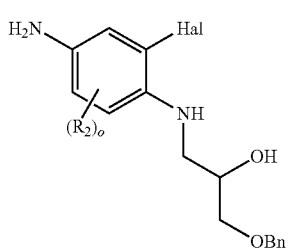

5a c) reacting compound 5a with compound 6:

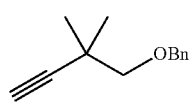

6 in the presence of a catalyst to form compound 7:

[Structure of compound 7: indole with H₂N, F, OBn, OH, OBn substituents]

d) reacting compound 7 with compound 8:

[Structure of compound 8: difluorobenzodioxole-cyclopropane-acyl chloride]

to form compound 9:

[Structure of compound 9]

and e) removing the two Bn protecting groups to form Compound 1.

In another embodiment, the invention features the above method wherein in step a), the brominating agent is N-bromosuccinimide.

In another embodiment, the invention features the above method wherein in step b), the reduction is carried out with hydrogen.

In another embodiment, the invention features the above method wherein in step b), the base is an inorganic base.

In another embodiment, the invention features the above method wherein in step b), the base is NaHCO₃.

In another embodiment, the invention features the above method wherein in step c), the catalyst is a palladium catalyst. In another embodiment, in step c), the catalyst is selected from palladium(II)acetate, Pd(dppf)Cl₂, Pd(dba)₂, tetrakis(triphenylphosphine)palladium(0) or tris(dibenzylideneacetone)dipalladium(0). In another embodiment, in step c), the catalyst is palladium(II)acetate.

In another embodiment, the invention features the above method wherein in step d), compound 8 is made in situ by halogenating the acid precursor without isolation.

In another embodiment, the invention features the above method wherein in step e), the Bn protecting groups are removed by hydrogenation.

In another aspect, the invention features a compound of formula 23:

[Structure of formula 23]

wherein:
  ring A is a fused cycloalkyl, heterocycloalkyl, aryl, or heteroaryl ring;
  $R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
  $R^J$ is hydrogen or $C_{1-6}$ aliphatic;
  X is CN or $CO_2R$;
  R is $C_{1-6}$ aliphatic or aryl; and
  m is an integer from 0 to 3 inclusive.

In another embodiment, the invention features a compound of formula 23 and the attendant definitions, wherein ring A is a fused heterocycloalkyl or heteroaryl. In another embodiment, ring A is selected from

[Structures of various fused ring systems]

In another embodiment, ring A is

[Structure of difluorodioxole ring]

In another embodiment, the invention features a compound of formula 23 and the attendant definitions, wherein X is CN. In another embodiment, X is CO$_2$Et.

In another embodiment, the invention features a compound of formula 23 and the attendant definitions, wherein m is 0.

In another embodiment, the invention features a compound of formula 23 and the attendant definitions, wherein R$^J$ is C$_{1-6}$ aliphatic. In another embodiment, R$^J$ is —CH$_2$CH$_3$.

In another aspect, the invention features the compound

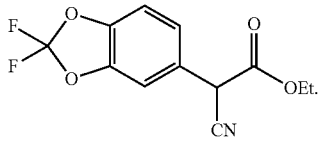 [SMILES: CCOC(=O)C(C#N)c1ccc2c(c1)OC(F)(F)O2]

In another aspect, the invention features the compound

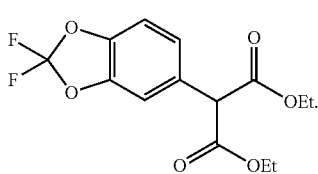 [SMILES: CCOC(=O)C(C(=O)OCC)c1ccc2c(c1)OC(F)(F)O2]

Methods of Preparing Compounds of Formulas I, II, III, and IV

Compounds of formulas I, II, II, and IV may be prepared by the methods of Schemes 1-3.

wherein ring A, R$_1$, m, X, R$^J$, Hal, q, and n are as defined above.

In Scheme 1, aryl halide IA is reacted with ester IB in the presence of a transition metal catalyst in a suitable solvent (e.g. toluene) to produce ester IC. In esters IB and IC, X can either be CN or CO$_2$R. Treatment of IC with an acid in a suitable solvent (e.g. dimethyl sulfoxide (DMSO)) produces I. Reaction of I with the dihalide IID in the presence of base gives the cycloalkylidene IIE. Hydrolization of the cyanide or remaining ester group depending on the identity of X gives the carboxylic acid IIF which is halogenated to yield the acid halide II.

In one embodiment, IA is commercially available. In one embodiment, ring A is a 5 membered dioxyl ring. In one embodiment, Hal in IA is Br. In one embodiment, the reaction of IA and IIB takes place in toluene in the presence of a Pd(0) caystalyst, e.g. Pd(dba)$_2$. In a further embodiment, the reaction takes place in the presence of an alkyl phosphine, e.g. t-Bu$_3$P and phosphate salt, e.g. Na$_3$PO$_4$. In another embodiment, the reaction of IA and IIB takes place at about 70° C. In another embodiment, R$^J$ is Et.

In one embodiment, the de-esterification of IC to I is done with an inorganic acid. In a further embodiment, the inorganic acid is HCl. The conversion takes place in an appropriate aprotic solvent (e.g. DMSO) at about 75° C.

In one embodiment, I is reacted with NaOH and an alkyl dihalide to yield the cycloalkylidene in a suitable solvent (e.g. MTBE). The process is adaptable to several spirocyclic rings by choosing the appropriate alkyl dihalide. For example, a spirocyclic butane ring can be produced by reacting I with, for example, 1-bromo-3-chloropropane. It has been found that a mixed bromo and chloro dihalide Scheme 1. Compounds of formula I and II.

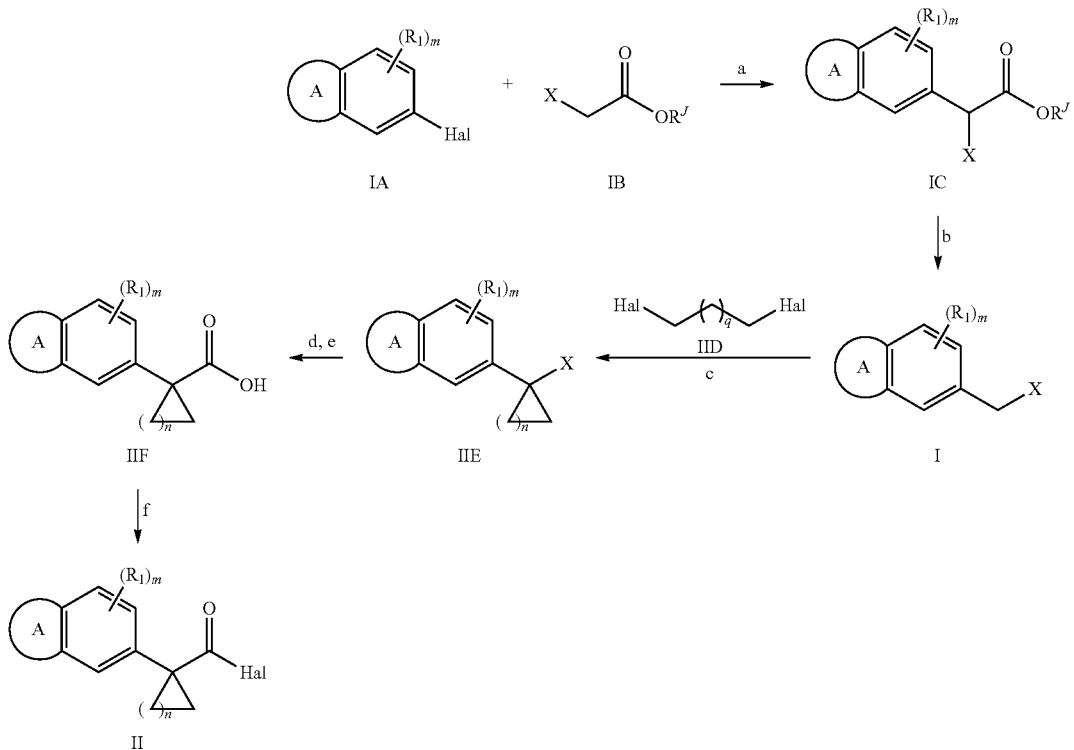

a = Pd(0) catalyst; b = acid; c = base; d = hydroxide base; e = acid; f = halogenating agent;

works best on an economic scale as it is believed that the thermodynamics of the reaction are more favorable.

In one embodiment, IIE is hydrolized to the carboxylic acid IIF in the presence of water and a base (e.g. NaOH) in a suitable solvent (e.g. ethanol). Subsequent treatment with an acid such as HCl yields IIF. In another embodiment, IIF is worked up by recrystallizing it from toluene.

In one embodiment, the halogenating agent that converts IIF to II is thionyl chloride. In another embodiment, the thionyl chloride is added to IIF in toluene at about 60° C. In one embodiment, this step directly proceeds the coupling between II and amine III (see below) and is carried out in the same reaction vessel.

There are several non-limiting advantages to forming II according to Scheme 1 and the embodiments described above and elsewhere in the application. These advantages are apparent even more so when manufacturing II on an economic scale and include the following. The overall reaction requires only 5 steps, which is less than what's been previously reported (i.e. starting from an aryl carboxylic acid, which is reduced to the methyl alcohol, which is converted to a methyl chloride, which is reacted with NaCN). This synthetic route introduces the CN or ester group (i.e. X) without a separate chlorinating reaction. Using ethanol as the cosolvent in hydrolyzing IIE to IIF results in a homogeneous reaction mixture making sampling and monitoring the reaction easier. Recrystallizing IIF from toluene eliminates the need for forming a dicyclohexylamine (DCA) salt as previously reported.

IIIB to form IIID. In one embodiment, the protecting group, P, in IIIC is benzyl (Bn). In another embodiment epoxide IIIC is chiral. In one embodiment IIIC is (R) IIIC. In another embodiment, IIIC is (S) IIIC. In one embodiment, the ring opening reaction is carried out in a suitable solvent (e.g. toluene) at about 80° C. In another embodiment, the ring opening reaction takes place in the presence of a Zn(II) catalyst (e.g. $Zn(ClO_4)_2$). In another embodiment, the conversion from IIIB to IIID comprises the ring opening reaction with epoxide IIIC, followed by hydrogenation, and then treatment with an acid to form IIID. In a further embodiment, hydrogenation is carried out with $H_2$/Pt(S)/C. In a further embodiment, the acid is toluene sulfonic acid, such that $A^\ominus$ is a tosylate anion.

In another embodiment, alkyne IIIE is coupled with IIID in a suitable solvent (e.g. acetonitrile) at about 80° C. In another embodiment, the coupling reaction takes place in the presence of a Pd(II) catalyst, such as $Pd(OAc)_2$. The initial reaction does not result in ring closure, only replacement of the halide on IIID. Ring closure is accomplished through reaction with another Pd(II) catalyst, such as $(MeCN)_2PdCl_2$ in a suitable solvent (e.g. acetonitrile). In one embodiment, ring closure takes place at about 80° C. In one embodiment, $R_3$ in alkyne IIIE is $—C(CH_3)_2CH_2OBn$. In one embodiment, the product from the coupling reaction is not isolated but taken up in acetonitrile and reacted with $(MeCN)_2PdCl_2$.

There are several non-limiting advantages to forming compound III according to Scheme 2 and the embodiments described above and elsewhere in the application. These

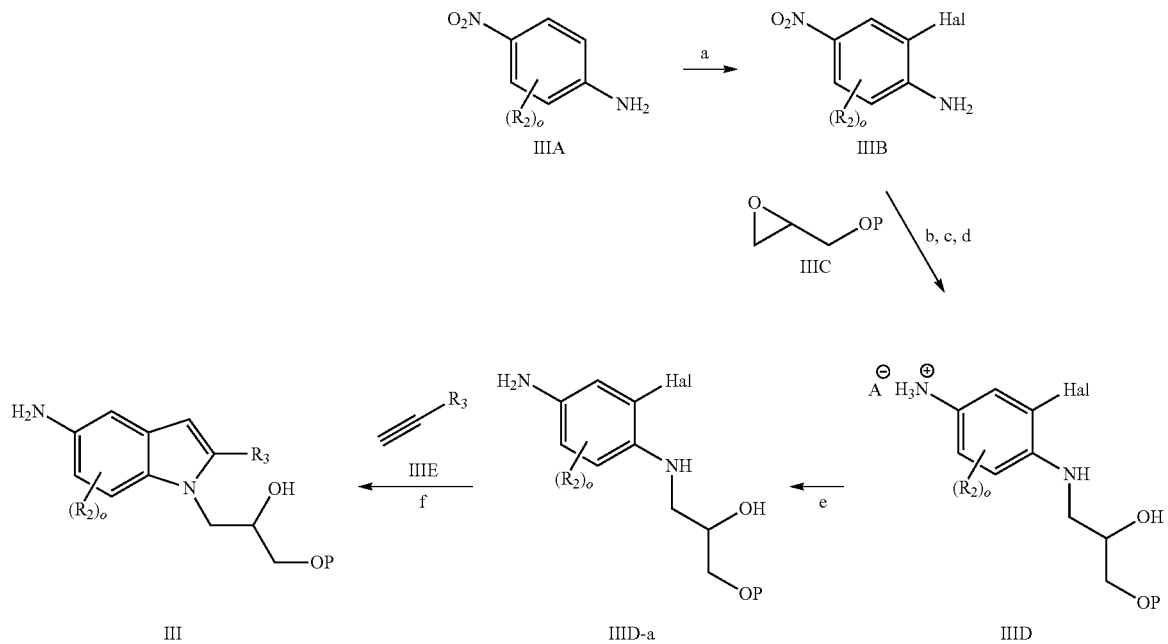

a = halogenating agent; b = ZN(II) catalyst; c = $H_2$, Pt; d = acid; e = base; f = Pd(II) catalyst;

wherein $R_2$, o, Hal, $A^\ominus$, and P are defined as above.

In one embodiment, in IIIA, $R_2$ is F and is meta to the amine group. In another embodiment, IIIA is brominated with N-bromosuccinimide in a suitable solvent (e.g. ethylacetate) at about 22° C.

In another embodiment, IIIB is reacted with epoxide IIIC effecting a ring opening reaction with the amine group of advantages are apparent even more so when manufacturing III on an economic scale and include the following. The overall number of steps have been reduced compared to what was disclosed previously to just 3 steps. Other advantages include the elimination of chromatography and byproducts from protecting groups.

Scheme 3. Compounds of Formula IV.

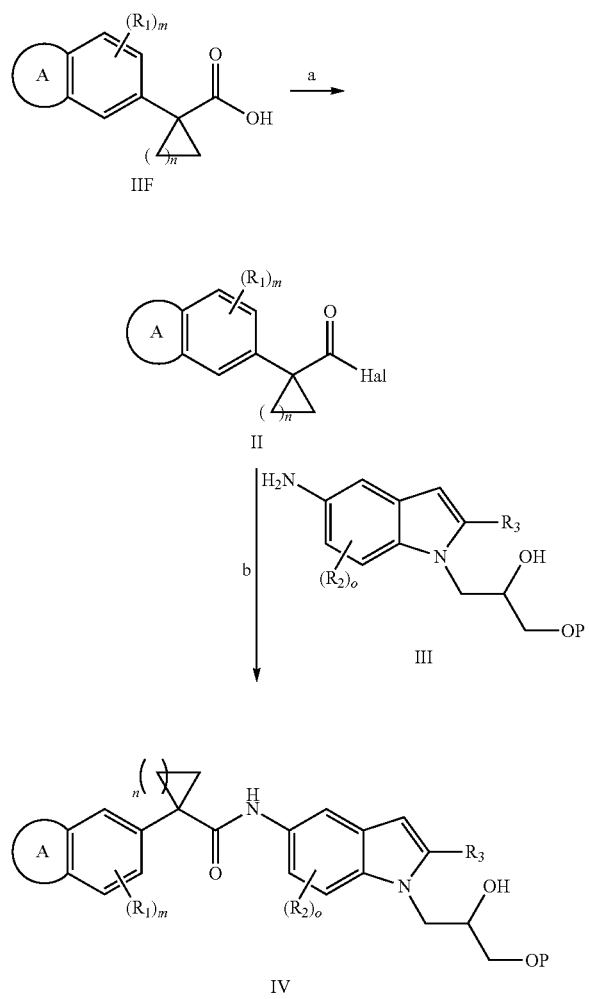

a = halogenating agent; b = aprotic solvent;

wherein ring A, $R_1$, m, n, hal, $R_2$, o, P, and $R_3$ are as defined above.

An acid-base reaction between II and III in a suitable solvent (e.g. dichloromethane (DCM)) yields the protected analog of Compound 1. In one embodiment, the acid halide II is prepared from IIF as depicted in Scheme 1 in the same reaction vessel and is not isolated. In another embodiment, the acid-based reaction is carried out in the presence of a base such as triethylamine (TEA). In one embodiment, the amount of TEA is 2 equivalents relative to II. In one embodiment, after a reaction time of about 4 hours at about 0° C. and warming to room temperature overnight, water is added to the mixture and stirred for an additional 30 minutes. The organic phase is separated and IV is isolated by distilling off the reaction solvent. In one embodiment, IV is collected by silica pad filtration.

In another embodiment, compounds of formula IV may be deprotected to form compounds of formula IVa according to Scheme 4.

Scheme 4. Deprotecting Compounds of Formula IV.

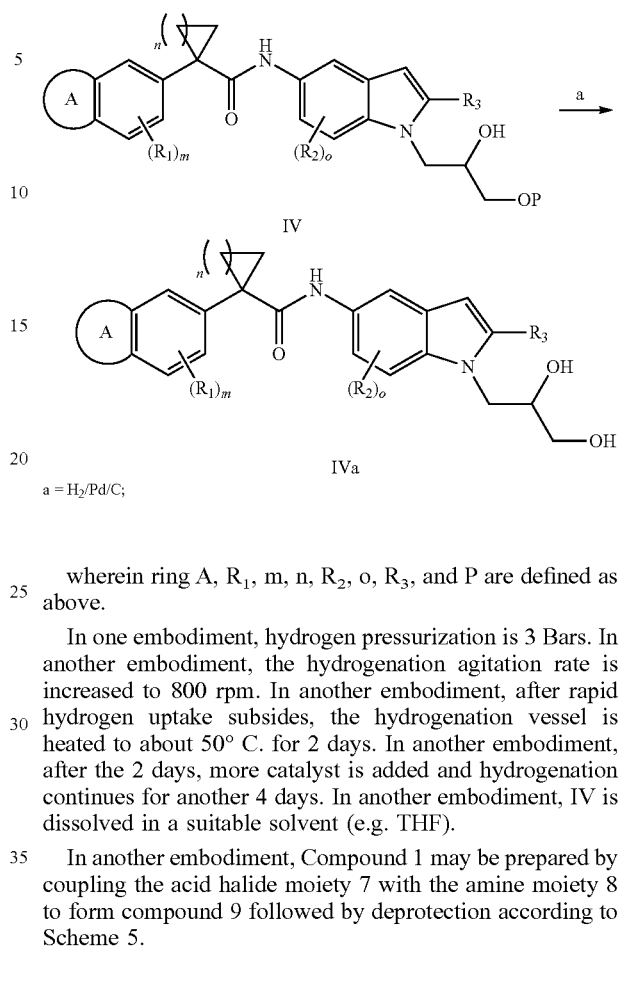

a = $H_2$/Pd/C;

wherein ring A, $R_1$, m, n, $R_2$, o, $R_3$, and P are defined as above.

In one embodiment, hydrogen pressurization is 3 Bars. In another embodiment, the hydrogenation agitation rate is increased to 800 rpm. In another embodiment, after rapid hydrogen uptake subsides, the hydrogenation vessel is heated to about 50° C. for 2 days. In another embodiment, after the 2 days, more catalyst is added and hydrogenation continues for another 4 days. In another embodiment, IV is dissolved in a suitable solvent (e.g. THF).

In another embodiment, Compound 1 may be prepared by coupling the acid halide moiety 7 with the amine moiety 8 to form compound 9 followed by deprotection according to Scheme 5.

Scheme 5. Preparation of Compound 1.

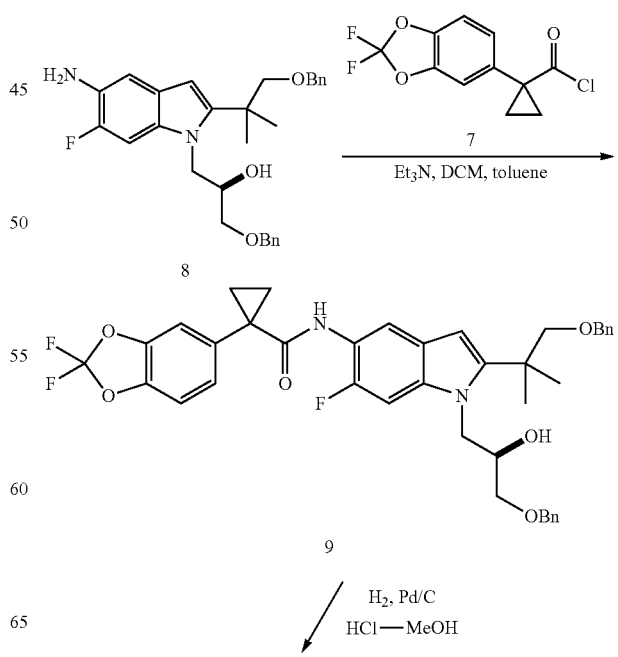

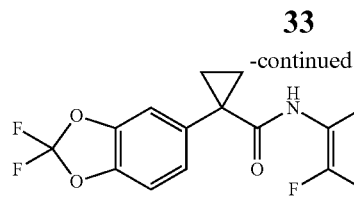
Compound 1
Wherein Compound 7 is prepared according to Scheme 6.
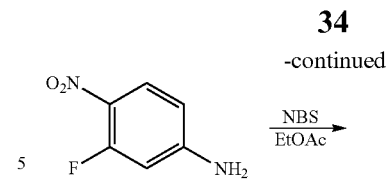
Scheme 6.
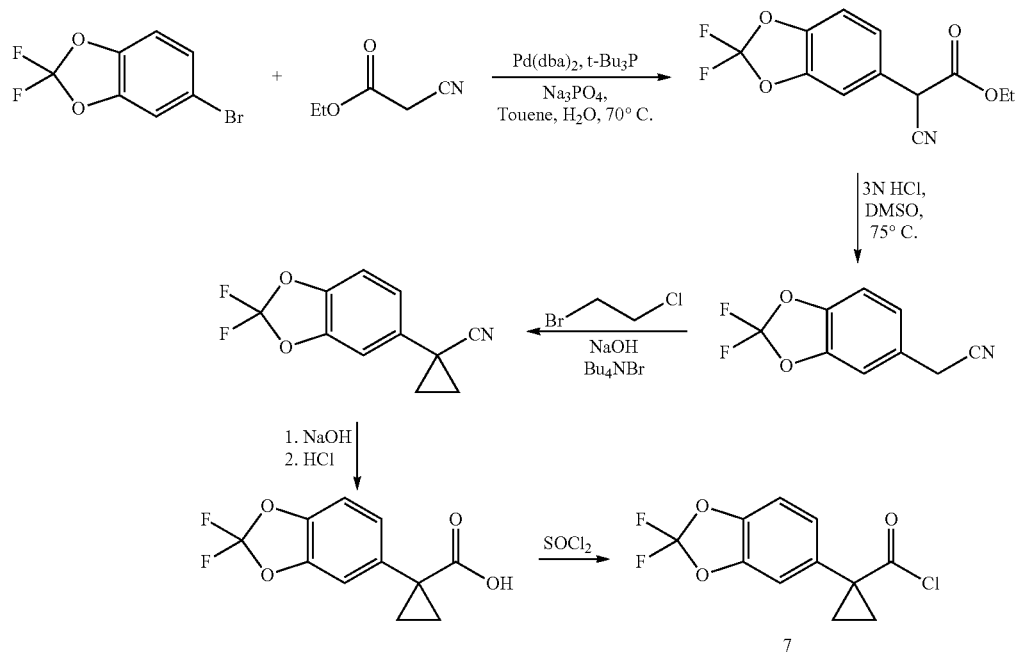
Wherein Compound 8 is prepared according to Scheme 7.
Scheme 7.
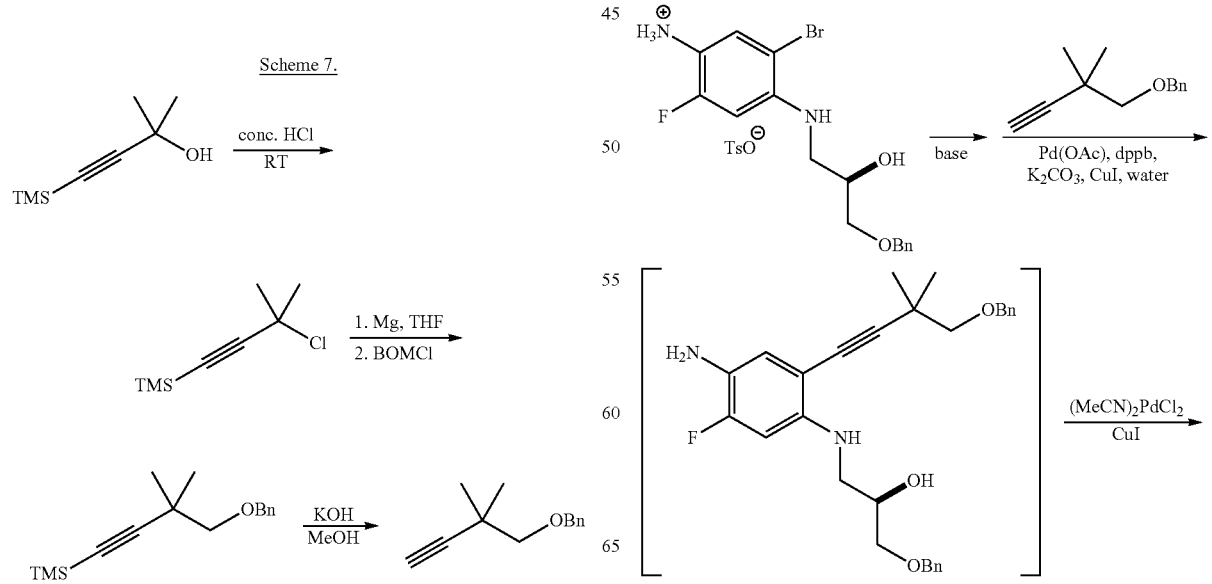

-continued

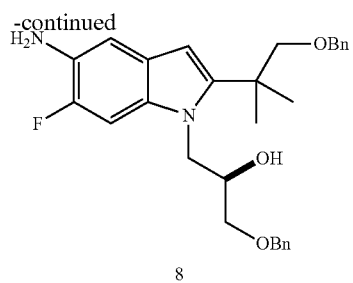

8

Uses, Formulation and Administration

Pharmaceutically Acceptable Compositions

In another aspect of the present invention, pharmaceutically acceptable compositions are provided, wherein these compositions comprise Compound 1 Form A or amorphous Compound 1 as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a Compound 1 described herein to a subject, preferably a mammal, in need thereof.

A "CFTR-mediated disease" as used herein is a disease selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia. In another embodiment, the CFTR mediated disease is cystic fibrosis, emphysema, COPD, or osteoporosis. In another embodiment, the CFTR mediated disease is cystic fibrosis.

In certain embodiments, the present invention provides a method of treating a CFTR-mediated disease in a human comprising the step of administering to said human an effective amount of a composition comprising Compound 1 described herein.

According to the invention an "effective amount" of Compound 1 Form A or amorphous Compound 1 or a pharmaceutically acceptable composition thereof is that amount effective for treating or lessening the severity of any of the diseases recited above.

Compound 1 or a pharmaceutically acceptable composition thereof may be administered using any amount and any route of administration effective for treating or lessening the severity of one or more of the diseases recited above.

In certain embodiments, Compound 1 described herein or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In one embodiment, Compound 1 described herein or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1 described herein or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient" or "subject", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In certain embodiments, the dosage amount of Compound 1 in the dosage unit form is from 100 mg to 1,000 mg. In another embodiment, the dosage amount of Compound 1 is from 200 mg to 900 mg. In another embodiment, the dosage amount of Compound 1 is from 300 mg to 800 mg. In another embodiment, the dosage amount of Compound 1 is from 400 mg to 700 mg. In another embodiment, the dosage amount of Compound 1 is from 500 mg to 600 mg.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h)

absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

It will also be appreciated that Compound 1 described herein or a pharmaceutically acceptable composition thereof can be employed in combination therapies, that is, Compound 1 can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl] oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than Compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), and N-(5-hydroxy-2,4-ditert-butyl-phenyl)-4-oxo-1H-quinoline-3-carboxamide.

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound disclosed in WO 2004028480, WO 2004110352, WO 2005094374, WO 2005120497, or WO 2006101740.

In another embodiment, the additional agent is a benzo (c)quinolizinium derivative that exhibits CFTR modulation activity or a benzopyran derivative that exhibits CFTR modulation activity.

In another embodiment, the additional agent is a compound disclosed in U.S. Pat. No. 7,202,262, U.S. Pat. No. 6,992,096, US20060148864, US20060148863, US20060035943, US20050164973, WO2006110483, WO2006044456, WO2006044682, WO2006044505, WO2006044503, WO2006044502, or WO2004091502.

In another embodiment, the additional agent is a compound disclosed in WO2004080972, WO2004111014, WO2005035514, WO2005049018, WO2006099256, WO2006127588, or WO2007044560.

These combinations are useful for treating the diseases described herein including cystic fibrosis. These combinations are also useful in the kits described herein.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In order that the invention described herein may be more fully understood, the following examples are set forth. It should be understood that these examples are for illustrative purposes only and are not to be construed as limiting this invention in any manner.

EXAMPLES

Methods & Materials

Vitride® (sodium bis(2-methoxyethoxy)aluminum hydride [or $NaAlH_2(OCH_2CH_2OCH_3)_2$], 65 wgt % solution in toluene) was purchased from Aldrich Chemicals. 3-Fluoro-4-nitroaniline was purchased from Capot Chemicals. 5-Bromo-2,2-difluoro-1,3-benzodioxole was purchased from Alfa Aesar. 2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Synthesis of Compound 1

Acid Moiety

Synthesis of (2,2-difluoro-1,3-benzodioxol-5-yl)-1-ethylacetate-acetonitrile

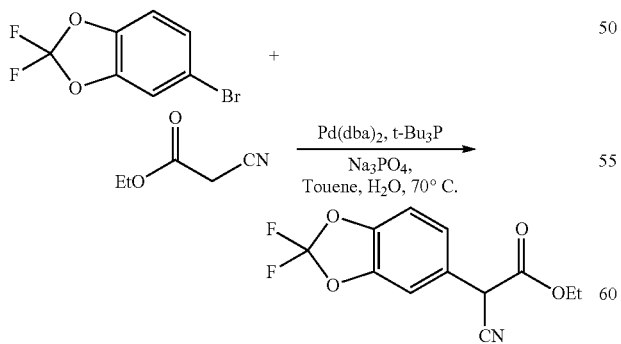

A reactor was purged with nitrogen and charged with 900 mL of toluene. The solvent was degassed via nitrogen sparge for no less than 16 h. To the reactor was then charged $Na_3PO_4$ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. $^1$H NMR (500 MHz, $CDCl_3$) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile

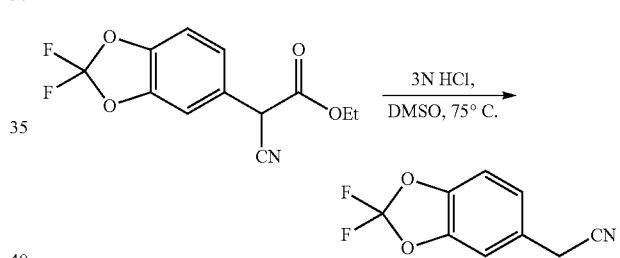

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature <40° C. The mixture was then heated to 75° C. over 1 h and analyzed by HPLC every 1-2 h for % conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Synthesis of (2,2-difluoro-1,3-benzodioxol-5-yl)-cyclopropanecarbonitrile

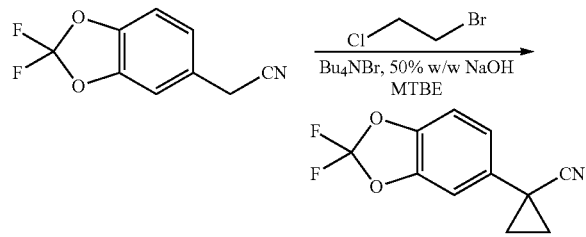

A stock solution of 50% w/w NaOH was degassed via nitrogen sparge for no less than 16 h. An appropriate amount of MTBE was similarly degassed for several hours. To a reactor purged with nitrogen was charged degassed MTBE (143 mL) followed by (2,2-difluoro-1,3-benzodioxol-5-yl)-acetonitrile (40.95 g, 207.7 mmol) and tetrabutylammonium bromide (2.25 g, 10.38 mmol). The volume of the mixture was noted and the mixture was degassed via nitrogen sparge for 30 min. Enough degassed MTBE is charged to return the mixture to the original volume prior to degassing. To the stirring mixture at 23.0° C. was charged degassed 50% w/w NaOH (143 mL) over 10 min followed by 1-bromo-2-chloroethane (44.7 g, 311.6 mmol) over 30 min. The reaction was analyzed by HPLC in 1 h intervals for % conversion. Before sampling, stirring was stopped and the phases allowed to separate. The top organic phase was sampled for analysis. When a % conversion >99% was observed (typically after 2.5-3 h), the reaction mixture was cooled to 10° C. and was charged with water (461 mL) at such a rate as to maintain a temperature <25° C. The temperature was adjusted to 20-25° C. and the phases separated. Note: sufficient time should be allowed for complete phase separation. The aqueous phase was extracted with MTBE (123 mL), and the combined organic phase was washed with 1 N HCl (163 mL) and 5% NaCl (163 mL). The solution of (2,2-difluoro-1,3-benzodioxol-5-yl)-cyclopropanecarbonitrile in MTBE was concentrated to 164 mL under vacuum at 40-50° C. The solution was charged with ethanol (256 mL) and again concentrated to 164 mL under vacuum at 50-60° C. Ethanol (256 mL) was charged and the mixture concentrated to 164 mL under vacuum at 50-60° C. The resulting mixture was cooled to 20-25° C. and diluted with ethanol to 266 mL in preparation for the next step. $^1$H NMR (500 MHz, DMSO) δ 7.43 (d, J=8.4 Hz, 1H), 7.40 (d, J=1.9 Hz, 1H), 7.30 (dd, J=8.4, 1.9 Hz, 1H), 1.75 (m, 2H), 1.53 (m, 2H).

Synthesis of 1-(2,2-difluoro-1,3-benzodioxol-5-yl)-cyclopropanecarboxylic acid

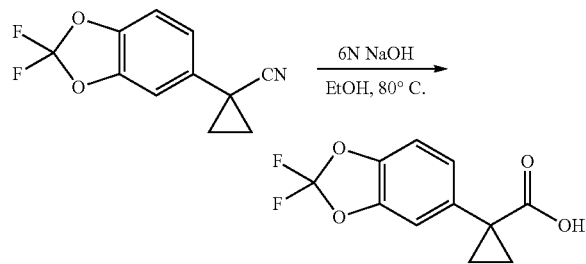

The solution of (2,2-difluoro-1,3-benzodioxol-5-yl)-cyclopropanecarbonitrile in ethanol from the previous step was charged with 6 N NaOH (277 mL) over 20 min and heated to an internal temperature of 77-78° C. over 45 min. The reaction progress was monitored by HPLC after 16 h. Note: the consumption of both (2,2-difluoro-1,3-benzodioxol-5-yl)-cyclopropanecarbonitrile and the primary amide resulting from partial hydrolysis of (2,2-difluoro-1,3-benzodioxol-5-yl)-cyclopropanecarbonitrile were monitored. When a % conversion >99% was observed (typically 100% conversion after 16 h), the reaction mixture was cooled to 25° C. and charged with ethanol (41 mL) and DCM (164 mL). The solution was cooled to 10° C. and charged with 6 N HCl (290 mL) at such a rate as to maintain a temperature <25° C. After warming to 20-25° C., the phases were allowed to separate. The bottom organic phase was collected and the top aqueous phase was back extracted with DCM (164 mL). Note: the aqueous phase was somewhat cloudy before and after the extraction due to a high concentration of inorganic salts. The organics were combined and concentrated under vacuum to 164 mL. Toluene (328 mL) was charged and the mixture condensed to 164 mL at 70-75° C. The mixture was cooled to 45° C., charged with MTBE (364 mL) and stirred at 60° C. for 20 min. The solution was cooled to 25° C. and polish filtered to remove residual inorganic salts. MTBE (123 mL) was used to rinse the reactor and the collected solids. The combined organics were transferred to a clean reactor in preparation for the next step.

Isolation of 1-(2,2-difluoro-1,3-benzodioxol-5-yl)-cyclopropanecarboxylic acid

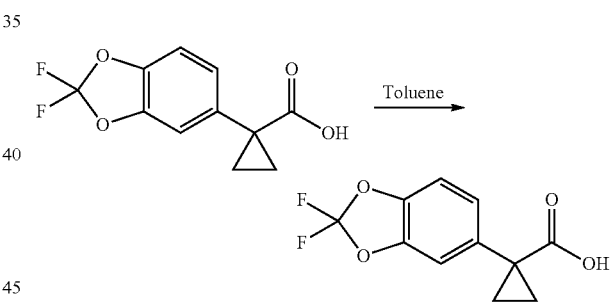

The solution of 1-(2,2-difluoro-1,3-benzodioxol-5-yl)-cyclopropanecarboxylic acid from the previous step is concentrated under vacuum to 164 mL, charged with toluene (328 mL) and concentrated to 164 mL at 70-75° C. The mixture was then heated to 100-105° C. to give a homogeneous solution. After stirring at that temperature for 30 min, the solution was cooled to 5° C. over 2 hours and maintained at 5° C. for 3 hours. The mixture was then filtered and the reactor and collected solid washed with cold 1:1 toluene/n-heptane (2×123 mL). The material was dried under vacuum at 55° C. for 17 hours to provide 1-(2,2-difluoro-1,3-benzodioxol-5-yl)-cyclopropanecarboxylic acid as an off-white crystalline solid. 1-(2,2-difluoro-1,3-benzodioxol-5-yl)-cyclopropanecarboxylic acid was isolated in 79% yield from (2,2-difluoro-1,3-benzodioxol-5-yl)-acetonitrile (3 steps including isolation) and with an HPLC purity of 99.0% AUC. ESI-MS m/z calc. 242.04. found 241.58 (M+1)+; $^1$H NMR (500 MHz, DMSO) δ 12.40 (s, 1H), 7.40 (d, J=1.6 Hz, 1H), 7.30 (d, J=8.3 Hz, 1H), 7.17 (dd, J=8.3, 1.7 Hz, 1H), 1.46 (m, 2H), 1.17 (m, 2H).

Alternative Synthesis of the Acid Moiety

Synthesis of (2,2-difluoro-1,3-benzodioxol-5-yl)-methanol

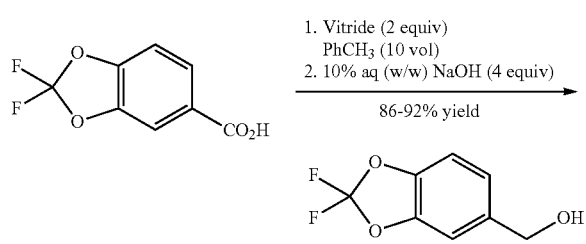

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully added via addition funnel maintaining the temperature at 40-50° C. After stirring for an additional 30 minutes, the layers are allowed to separate at 40° C. The organic phase is cooled to 20° C. then washed with water (2×1.5 vol), dried (Na$_2$SO$_4$), filtered, and concentrated to afford crude (2,2-difluoro-1,3-benzodioxol-5-yl)-methanol that is used directly in the next step.

Synthesis of 5-chloromethyl-2,2-difluoro-1,3-benzodioxole

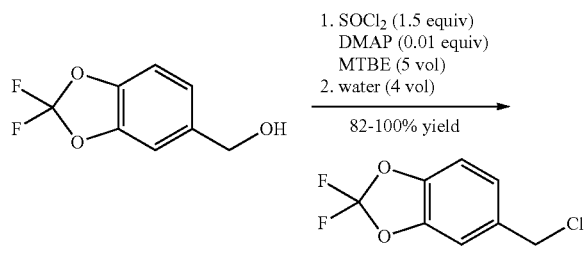

(2,2-difluoro-1,3-benzodioxol-5-yl)-methanol (1.0 eq) is dissolved in MTBE (5 vol). A catalytic amount of DMAP (1 mol %) is added and SOCl$_2$ (1.2 eq) is added via addition funnel. The SOCl$_2$ is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried (Na$_2$SO$_4$), filtered, and concentrated to afford crude 5-chloromethyl-2,2-difluoro-1,3-benzodioxole that is used directly in the next step.

Synthesis of (2,2-difluoro-1,3-benzodioxol-5-yl)-acetonitrile

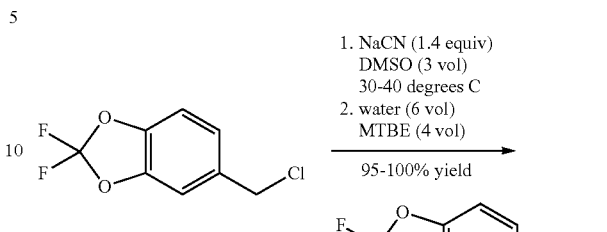

A solution of 5-chloromethyl-2,2-difluoro-1,3-benzodioxole (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried (Na$_2$SO$_4$), filtered, and concentrated to afford crude (2,2-difluoro-1,3-benzodioxol-5-yl)-acetonitrile (95%) that is used directly in the next step.

The remaining steps are the same as described above for the synthesis of the acid moiety.

Amine Moiety

Synthesis of 2-bromo-5-fluoro-4-nitroaniline

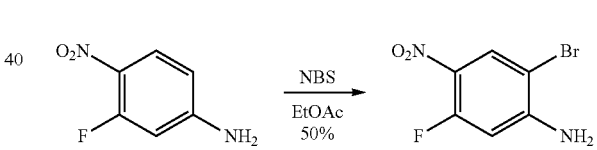

A flask was charged with 3-fluoro-4-nitroaniline (1.0 equiv) followed by ethyl acetate (10 vol) and stirred to dissolve all solids. N-Bromosuccinimide (1.0 equiv) was added as a portion-wise as to maintain internal temperature of 22° C. At the end of the reaction, the reaction mixture was concentrated in vacuo on a rotavap. The residue was slurried in distilled water (5 vol) to dissolve and remove succinimide. (The succinimide can also be removed by water workup procedure.) The water was decanted and the solid was slurried in 2-propanol (5 vol) overnight. The resulting slurry was filtered and the wetcake was washed with 2-propanol, dried in vacuum oven at 50° C. overnight with N$_2$ bleed until constant weight was achieved. A yellowish tan solid was isolated (50% yield, 97.5% AUC). Other impurities were a bromo-regioisomer (1.4% AUC) and a di-bromo adduct (1.1% AUC). $^1$H NMR (500 MHz, DMSO)

δ 8.19 (1H, d, J=8.1 Hz), 7.06 (br. s, 2H), 6.64 (d, 1H, J=14.3 Hz).

Synthesis of p-toluenesulfonic acid salt of (R)-1-((4-amino-2-bromo-5-fluorophenyl)amino)-3-(benzyloxy)propan-2-ol

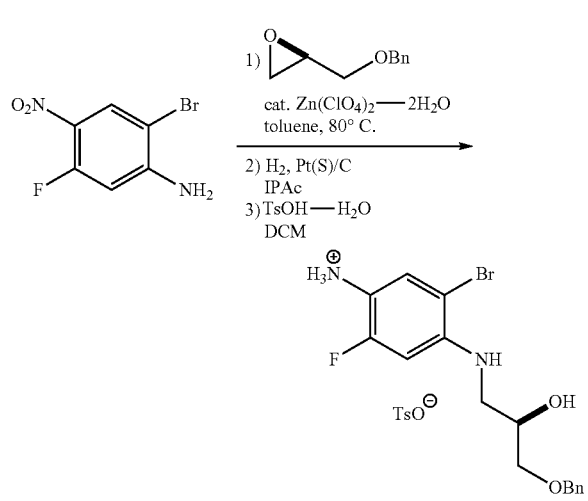

A thoroughly dried flask under $N_2$ was charged with the following: Activated powdered 4A molecular sieves (50 wt % based on 2-bromo-5-fluoro-4-nitroaniline), 2-Bromo-5-fluoro-4-nitroaniline (1.0 equiv), zinc perchlorate dihydrate (20 mol %), and toluene (8 vol). The mixture was stirred at room temperature for NMT 30 min. Lastly, (R)-benzyl glycidyl ether (2.0 equiv) in toluene (2 vol) was added in a steady stream. The reaction was heated to 80° C. (internal temperature) and stirred for approximately 7 hours or until 2-Bromo-5-fluoro-4-nitroaniline was <5% AUC.

The reaction was cooled to room temperature and Celite (50 wt %) was added, followed by ethyl acetate (10 vol). The resulting mixture was filtered to remove Celite and sieves and washed with ethyl acetate (2 vol). The filtrate was washed with ammonium chloride solution (4 vol, 20% w/v). The organic layer was washed with sodium bicarbonate solution (4 vol×2.5% w/v). The organic layer was concentrated in vacuo on a rotovap. The resulting slurry was dissolved in isopropyl acetate (10 vol) and this solution was transferred to a Buchi hydrogenator.

The hydrogenator was charged with 5 wt % Pt(S)/C (1.5 mol %) and the mixture was stirred under $N_2$ at 30° C. (internal temperature). The reaction was flushed with $N_2$ followed by hydrogen. The hydrogenator pressure was adjusted to 1 Bar of hydrogen and the mixture was stirred rapidly (>1200 rpm). At the end of the reaction, the catalyst was filtered through a pad of Celite and washed with dichloromethane (10 vol). The filtrate was concentrated in vacuo. Any remaining isopropyl acetate was chased with dichloromethane (2 vol) and concentrated on a rotavap to dryness.

The resulting residue was dissolved in dichloromethane (10 vol). p-Toluenesulfonic acid monohydrate (1.2 equiv) was added and stirred overnight. The product was filtered and washed with dichloromethane (2 vol) and suction dried. The wetcake was transferred to drying trays and into a vacuum oven and dried at 45° C. with $N_2$ bleed until constant weight was achieved. p-Toluenesulfonic acid salt of (R)-1-((4-amino-2-bromo-5-fluorophenyl)amino)-3-(benzyloxy)propan-2-ol was isolated as an off-white solid.
in the presence of a catalyst to form compound 7:
Chiral purity was determined to be >97% ee.

Synthesis of (3-Chloro-3-methylbut-1-ynyl)trimethylsilane

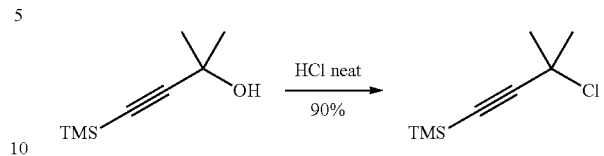

Propargyl alcohol (1.0 equiv) was charged to a vessel. Aqueous hydrochloric acid (37%, 3.75 vol) was added and stirring begun. During dissolution of the solid alcohol, a modest endotherm (5-6° C.) is observed. The resulting mixture was stirred overnight (16 h), slowly becoming dark red. A 30 L jacketed vessel is charged with water (5 vol) which is then cooled to 10° C. The reaction mixture is transferred slowly into the water by vacuum, maintaining the internal temperature of the mixture below 25° C. Hexanes (3 vol) is added and the resulting mixture is stirred for 0.5 h. The phases were settled and the aqueous phase (pH<1) was drained off and discarded. The organic phase was concentrated in vacuo using a rotary evaporator, furnishing the product as red oil.

Synthesis of (4-(Benzyloxy)-3,3-dimethylbut-1-ynyl)trimethylsilane

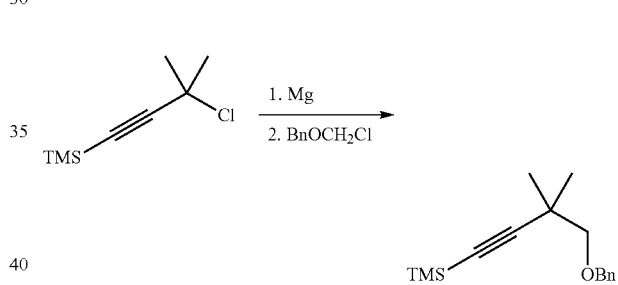

Method A

All equivalent and volume descriptors in this part are based on a 250 g reaction. Magnesium turnings (69.5 g, 2.86 mol, 2.0 equiv) were charged to a 3 L 4-neck reactor and stirred with a magnetic stirrer under nitrogen for 0.5 h. The reactor was immersed in an ice-water bath. A solution of the propargyl chloride (250 g, 1.43 mol, 1.0 equiv) in THF (1.8 L, 7.2 vol) was added slowly to the reactor, with stirring, until an initial exotherm (~10° C.) was observed. The Grignard reagent formation was confirmed by IPC using $^1$H-NMR spectroscopy. Once the exotherm subsided, the remainder of the solution was added slowly, maintaining the batch temperature <15° C. The addition required ~3.5 h. The resulting dark green mixture was decanted into a 2 L capped bottle.

All equivalent and volume descriptors in this part are based on a 500 g reaction. A 22 L reactor was charged with a solution of benzyl chloromethyl ether (95%, 375 g, 2.31 mol, 0.8 equiv) in THF (1.5 L, 3 vol). The reactor was cooled in an ice-water bath. Two Grignard reagent batches prepared as described above were combined and then added slowly to the benzyl chloromethyl ether solution via an addition funnel, maintaining the batch temperature below 25° C. The addition required 1.5 h. The reaction mixture was stirred overnight (16 h).

All equivalent and volume descriptors in this part are based on a 1 kg reaction. A solution of 15% ammonium chloride was prepared in a 30 L jacketed reactor (1.5 kg in 8.5 kg of water, 10 vol). The solution was cooled to 5° C. Two Grignard reaction mixtures prepared as described above were combined and then transferred into the ammonium chloride solution via a header vessel. An exotherm was observed in this quench, which was carried out at a rate such as to keep the internal temperature below 25° C. Once the transfer was complete, the vessel jacket temperature was set to 25° C. Hexanes (8 L, 8 vol) was added and the mixture was stirred for 0.5 h. After settling the phases, the aqueous phase (pH 9) was drained off and discarded. The remaining organic phase was washed with water (2 L, 2 vol). The organic phase was concentrated in vacuo using a 22 L rotary evaporator, providing the crude product as an orange oil.

Method B

Magnesium turnings (106 g, 4.35 mol, 1.0 eq) were charged to a 22 L reactor and then suspended in THF (760 mL, 1 vol). The vessel was cooled in an ice-water bath such that the batch temperature reached 2° C. A solution of the propargyl chloride (760 g, 4.35 mol, 1.0 equiv) in THF (4.5 L, 6 vol) was added slowly to the reactor. After 100 mL was added, the addition was stopped and the mixture stirred until a 13° C. exotherm was observed, indicating the Grignard reagent initiation. Once the exotherm subsided, another 500 mL of the propargyl chloride solution was added slowly, maintaining the batch temperature <20° C. The Grignard reagent formation was confirmed by IPC using $^1$H-NMR spectroscopy. The remainder of the propargyl chloride solution was added slowly, maintaining the batch temperature <20° C. The addition required ~1.5 h. The resulting dark green solution was stirred for 0.5 h. The Grignard reagent formation was confirmed by IPC using $^1$H-NMR spectroscopy. Neat benzyl chloromethyl ether was charged to the reactor addition funnel and then added dropwise into the reactor, maintaining the batch temperature below 25° C. The addition required 1.0 h. The reaction mixture was stirred overnight. The aqueous work-up and concentration was carried out using the same procedure and relative amounts of materials as in Method A to give the product as an orange oil.

Synthesis of 4-Benzyloxy-3,3-dimethylbut-1-yne

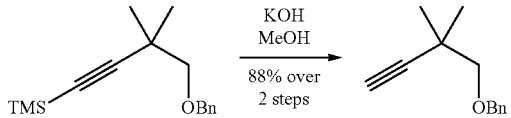 [SMILES: CC(C)(C#C[Si](C)(C)C)COCc1ccccc1 ; C#CC(C)(C)COCc1ccccc1]

A 30 L jacketed reactor was charged with methanol (6 vol) which was then cooled to 5° C. Potassium hydroxide (85%, 1.3 equiv) was added to the reactor. A 15-20° C. exotherm was observed as the potassium hydroxide dissolved. The jacket temperature was set to 25° C. A solution of 4-benzyloxy-3,3-dimethyl-1-trimethylsilylbut-1-yne (1.0 equiv) in methanol (2 vol) was added and the resulting mixture was stirred until reaction completion, as monitored by HPLC. Typical reaction time at 25° C. is 3-4 h. The reaction mixture is diluted with water (8 vol) and then stirred for 0.5 h. Hexanes (6 vol) was added and the resulting mixture was stirred for 0.5 h. The phases were allowed to settle and then the aqueous phase (pH 10-11) was drained off and discarded. The organic phase was washed with a solution of KOH (85%, 0.4 equiv) in water (8 vol) followed by water (8 vol).

The organic phase was then concentrated down using a rotary evaporator, yielding the title material as a yellow-orange oil. Typical purity of this material is in the 80% range with primarily a single impurity present. $^1$H NMR (400 MHz, C$_6$D$_6$) δ 7.28 (d, 2H, J=7.4 Hz), 7.18 (t, 2H, J=7.2 Hz), 7.10 (d, 1H, J=7.2 Hz), 4.35 (s, 2H), 3.24 (s, 2H), 1.91 (s, 1H), 1.25 (s, 6H).

Synthesis of N-benzylglycolated-5-amino-2-(2-benzyloxy-1,1-dimethylethyl)-6-fluoroindole Method A Synthesis of (R)-1-((4-amino-2-(4-(benzyloxy)-3,3-dimethylbut-1-yn-1-yl)-5-fluorophenyl)amino)-3-(benzyloxy)propan-2-ol

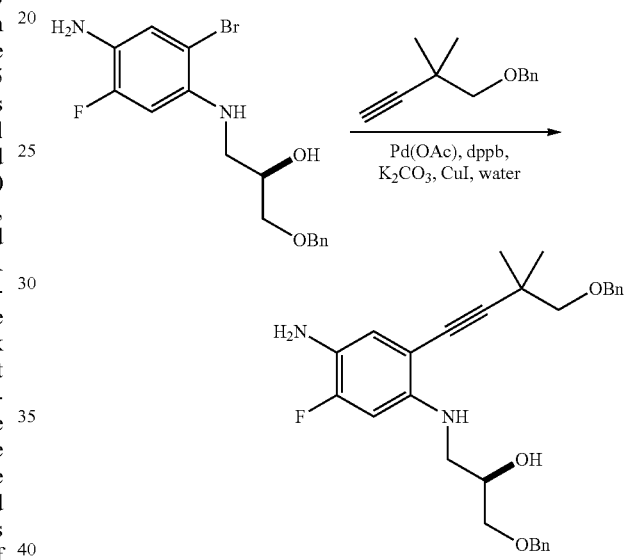

p-Toluenesulfonic acid salt of (R)-1-((4-amino-2-bromo-5-fluorophenyl)amino)-3-(benzyloxy)propan-2-ol was freebased by stirring the solid in dichloromethane (5 vol) and saturated NaHCO$_3$ solution (5 vol) until clear organic layer was achieved. The resulting layers were separated and the organic layer was washed with saturated NaHCO$_3$ solution (5 vol) followed by brine and concentrated in vacuo to obtain (R)-1-((4-amino-2-bromo-5-fluorophenyl)amino)-3-(benzyloxy)propan-2-ol free base as an oil.

Palladium acetate (0.01 eq), dppb (0.015 eq), CuI (0.015 eq) and potassium carbonate (3 eq) are suspended in acetonitrile (1.2 vol). After stirring for 15 minutes, a solution of 4-benzyloxy-3,3-dimethylbut-1-yne (1.1 eq) in acetonitrile (0.2 vol) is added. The mixture is sparged with nitrogen gas for 1 h and then a solution of (R)-1-((4-amino-2-bromo-5-fluorophenyl)amino)-3-(benzyloxy)propan-2-ol free base (1 eq) in acetonitrile (4.1 vol) is added. The mixture is sparged with nitrogen gas for another hour and then is heated to 80° C. Reaction progress is monitored by HPLC and the reaction is usually complete within 3-5 h. The mixture is cooled to room temperature and then filtered through Celite. The cake is washed with acetonitrile (4 vol). The combined filtrates are azeotroped to dryness and then the mixture is polish filtered into the next reactor. The acetonitrile solution of (R)-1-((4-amino-2-(4-(benzyloxy)-3,3-dimethylbut-1-yn-1- yl)-5-fluorophenyl)amino)-3-(benzyloxy)propan-2-ol thus obtained is used directly in the next procedure (cyclization) without further manipulation.

Synthesis of N-benzylglycolated-5-amino-2-(2-benzyloxy-1,1-dimethylethyl)-6-fluoroindole

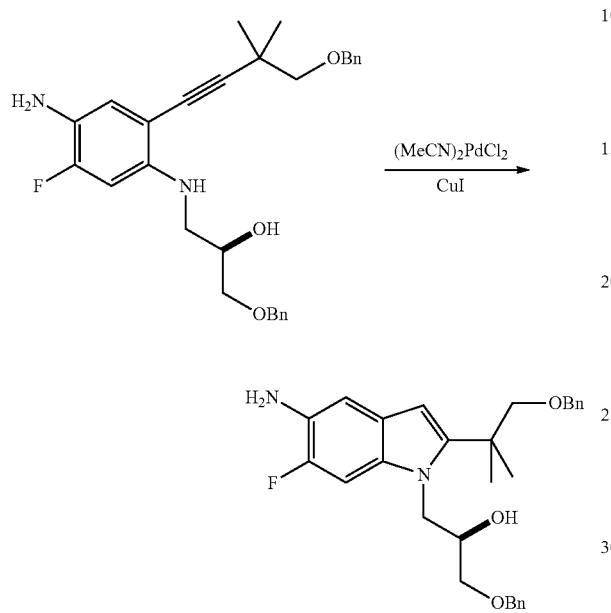

Bis-acetonitriledichloropalladium (0.1 eq) and CuI (0.1 eq) are charged to the reactor and then suspended in a solution of (R)-1-((4-amino-2-(4-(benzyloxy)-3,3-dimethylbut-1-yn-1-yl)-5-fluorophenyl)amino)-3-(benzyloxy)propan-2-ol obtained above (1 eq) in acetonitrile (9.5 vol total). The mixture is sparged with nitrogen gas for 1 h and then is heated to 80° C. The reaction progress is monitored by HPLC and the reaction is typically complete within 1-3 h. The mixture is filtered through Celite and the cake is washed with acetonitrile. A solvent swap into ethyl acetate (7.5 vol) is performed. The ethyl acetate solution is washed with aqueous $NH_3$—$NH_4Cl$ solution (2×2.5 vol) followed by 10% brine (2.5 vol). The ethyl acetate solution is then stirred with silica gel (1.8 wt eq) and Si-TMT (0.1 wt eq) for 6 h. After filtration, the resulting solution is concentrated down. The residual oil is dissolved in DCM/heptane (4 vol) and then purified by column chromatography. The oil thus obtained is then crystallized from 25% EtOAc/heptane (4 vol). Crystalline (R)-1-(5-amino-2-(1-(benzyloxy)-2-methylpropan-2-yl)-6-fluoro-1H-indol-1-yl)-3-(benzyloxy)propan-2-ol is typically obtained in 27-38% yield. $^1$H NMR (400 MHz, DMSO) δ 7.38-7.34 (m, 4H), 7.32-7.23 (m, 6H), 7.21 (d, 1H, J=12.8 Hz), 6.77 (d, 1H, J=9.0 Hz), 6.06 (s, 1H), 5.13 (d, 1H, J=4.9 Hz), 4.54 (s, 2H), 4.46 (br. s, 2H), 4.45 (s, 2H), 4.33 (d, 1H, J=12.4 Hz), 4.09-4.04 (m, 2H), 3.63 (d, 1H, J=9.2 Hz), 3.56 (d, 1H, J=9.2 Hz), 3.49 (dd, 1H, J=9.8, 4.4 Hz), 3.43 (dd, 1H, J=9.8, 5.7 Hz), 1.40 (s, 6H).

Synthesis of N-benzylglycolated-5-amino-2-(2-benzyloxy-1,1-dimethylethyl)-6-fluoroindole Method B

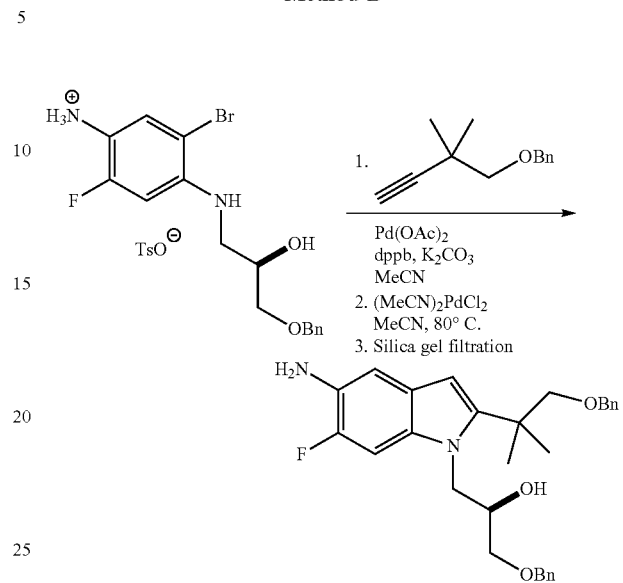

Palladium acetate (33 g, 0.04 eq), dppb (94 g, 0.06 eq), and potassium carbonate (1.5 kg, 3.0 eq) are charged to a reactor. The free based oil benzylglocolated 4-ammonium-2-bromo-5-flouroaniline (1.5 kg, 1.0 eq) was dissolved in acetonitrile (8.2 L, 4.1 vol) and then added to the reactor. The mixture was sparged with nitrogen gas for NLT 1 h. A solution of 4-benzyloxy-3,3-dimethylbut-1-yne (70%, 1.1 kg, 1.05 eq) in acetonitrile was added to the mixture which was then sparged with nitrogen gas for NLT 1 h. The mixture was heated to 80° C. and then stirred overnight. IPC by HPLC is carried out and the reaction is determined to be complete after 16 h. The mixture was cooled to ambient temperature and then filtered through a pad of Celite (228 g). The reactor and Celite pad were washed with acetonitrile (2×2 L, 2 vol). The combined phases are concentrated on a 22 L rotary evaporator until 8 L of solvent have been collected, leaving the crude product in 7 L (3.5 vol) of acetonitrile.

Bis-acetonitriledichloropalladium (144 g, 0.15 eq) was charged to the reactor. The crude solution was transferred back into the reactor and the roto-vap bulb was washed with acetonitrile (4 L, 2 vol). The combined solutions were sparged with nitrogen gas for NLT 1 h. The reaction mixture was heated to 80° C. for NLT 16 h. In process control by HPLC shows complete consumption of starting material. The reaction mixture was filtered through Celite (300 g). The reactor and filter cake were washed with acetonitrile (3 L, 1.5 vol). The combined filtrates were concentrated to an oil by rotary evaporation. The oil was dissolved in ethyl acetate (8.8 L, 4.4 vol). The solution was washed with 20% ammonium chloride (5 L, 2.5 vol) followed by 5% brine (5 L, 2.5 vol). Silica gel (3.5 kg, 1.8 wt. eq.) of silica gel was added to the organic phase, which was stirred overnight. Deloxan THP II metal scavenger (358 g) and heptane (17.6 L) were added and the resulting mixture was stirred for NLT 3 h. The mixture was filtered through a sintered glass funnel. The filter cake was washed with 30% ethyl acetate in heptane (25 L). The combined filtrates were concentrated under reduced pressure to give N-benzylglycolated-5-amino-2-(2-benzyloxy-1,1-dimethylethyl)-6-fluoroindole as a brown paste (1.4 kg).

Synthesis of Compound 1

Synthesis of benzyl protected Compound 1

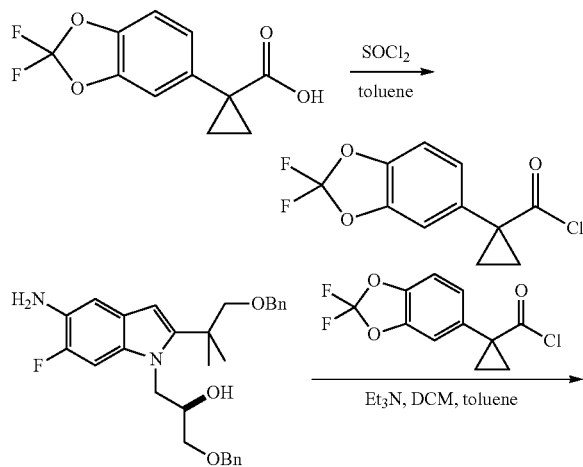

1-(2,2-Difluoro-1,3-benzodioxol-5-yl)-cyclopropanecarboxylic acid (1.3 equiv) was slurried in toluene (2.5 vol, based on 1-(2,2-difluoro-1,3-benzodioxol-5-yl)-cyclopropanecarboxylic acid). Thionyl chloride (SOCl$_2$, 1.7 equiv) was added via addition funnel. and the mixture was heated to 60° C. The resulting mixture was stirred for 2 h. The toluene and the excess SOCl2 were distilled off using rotavop. Additional toluene (2.5 vol, based on 1-(2,2-difluoro-1,3-benzodioxol-5-yl)-cyclopropanecarboxylic acid) was added and the mixture was distilled down to 1 vol of toluene. A solution of (R)-1-(5-amino-2-(1-(benzyloxy)-2-methylpropan-2-yl)-6-fluoro-1H-indol-1-yl)-3-(benzyloxy) propan-2-ol (1 eq) and triethylamine (3 eq) in DCM (4 vol) is cooled to 0° C. The acid chloride solution in toluene (1 vol) is added while maintaining the batch temperature below 10° C. The reaction progress is monitored by HPLC, and the reaction is usually complete within minutes. After warming to 25° C., the reaction mixture is washed with 5% NaHCO$_3$ (3.5 vol), 1 M NaOH (3.5 vol) and 1 M HCl (5 vol). A solvent swap to into methanol (2 vol) is performed and the resulting solution of (R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide in methanol is used without further manipulation in the next step (hydrogenolysis).

Synthesis of Compound 1

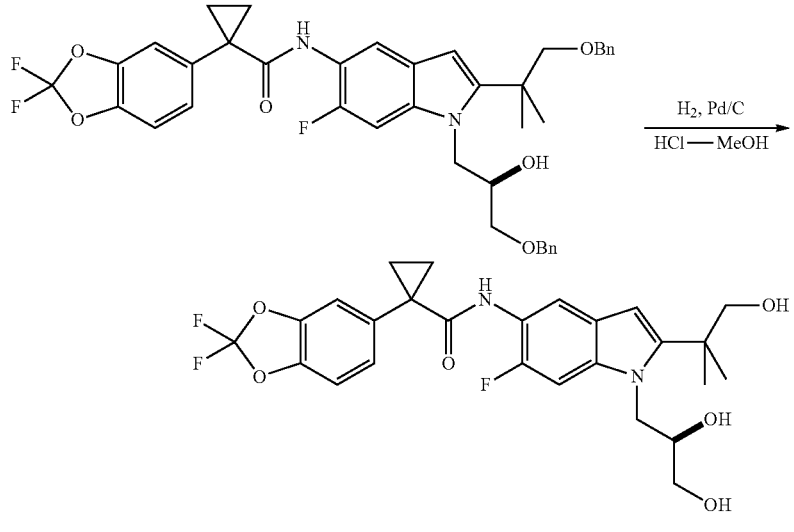

Compound 1

-continued

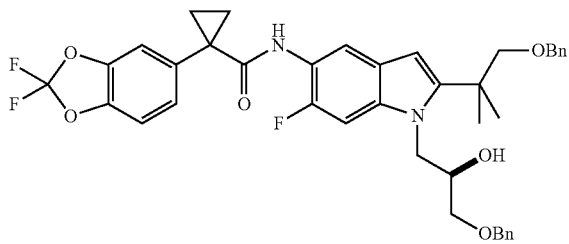

5% palladium on charcoal (~50% wet, 0.01 eq) is charged to an appropriate hydrogenation vessel. The (R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide solution in methanol (2 vol) obtained above is added carefully, followed by a 3 M solution of HCl in methanol. The vessel is purged with nitrogen gas and then with hydrogen gas. The mixture is stirred vigorously until the reaction is complete, as determined by HPLC analysis. Typical reaction time is 3-5 h. The reaction mixture is filtered through Celite and the cake is washed with methanol (2 vol). A solvent swap into isopropanol (3 vol) is performed. Crude VX-661 is crystallized from 75% IPA-heptane (4 vol, ie. 1 vol heptane added to the 3 vol of IPA) and the resulting crystals are matured in 50% IPA-heptane (ie. 2 vol of heptane added to the mixture). Typical yields of compound 4 from the two-step acylation/hydrogenolysis procedure range from 68% to 84%. Compound 4 can be recrystallized from IPA-heptane following the same procedure just described.

Compound 1 may also be prepared by one of several synthetic routes disclosed in US published patent application US20090131492, incorporated herein by reference.

Table 10 below recites analytical data for Compound 1.

TABLE 10

| Cmpd. No | LC/MS M + 1 | LC/RT min | NMR |
|---|---|---|---|
| 1 | 521.5 | 1.69 | 1H NMR (400.0 MHz, CD$_3$CN) d 7.69 (d, J = 7.7 Hz, 1H), 7.44 (d, J = 1.6 Hz, 1H), 7.39 (dd, J = 1.7, 8.3 Hz, 1H), 7.31 (s, 1H), 7.27 (d, J = 8.3 Hz, 1H), 7.20 (d, J = 12.0 Hz, 1H), 6.34 (s, 1H), 4.32 (d, J = 6.8 Hz, 2H), 4.15-4.09 (m, 1H), 3.89 (dd, J = 6.0, 11.5 Hz, 1H), 3.63-3.52 (m, 3H), 3.42 (d, J = 4.6 Hz, 1H), 3.21 (dd, J = 6.2, 7.2 Hz, 1H), 3.04 (t, J = 5.8 Hz, 1H), 1.59 (dd, J = 3.8, 6.8 Hz, 2H), 1.44 (s, 3H), 1.33 (s, 3H) and 1.18 (dd, J = 3.7, 6.8 Hz, 2H) ppm. |

Assays

Assays for Detecting and Measuring ΔF508-CFTR Correction Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying ΔF508-CFTR Modulation Properties of Compounds 1. Using Chamber Assay Using chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and Acq-Knowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), CaCl₂ (1.2), MgCl₂ (1.2), K₂HPO₄ (2.4), KHPO₄ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% CO₂ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 ρM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), MgCl₂ (1), HEPES (10), and 240 μg/ml amphotericin-B (pH adjusted to 7.35 with CsOH).

Extracellular solution (in mM): N-methyl-D-glucamine (NMDG)-Cl (150), MgCl₂ (2), CaCl₂ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% CO₂ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perfusion, the nonspecific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

12. Solutions

Extracellular solution (in mM): NMDG (150), aspartic acid (150), CaCl₂ (5), MgCl₂ (2), and HEPES (10) (pH adjusted to 7.35 with Tris base).

Intracellular solution (in mM): NMDG-Cl (150), MgCl₂ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% CO₂ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured and is shown in Table 11.

TABLE 11

| EC50 Bins: +++ <= 2.0 < ++ <= 5.0 < + | | |
| PercentActivity Bins: + <= 25.0 < ++ <= 100.0 < +++ | | |
| Cmpd. No. | Binned EC50 | Binned MaxEfficacy |
| --- | --- | --- |
| 1 | +++ | +++ |

We claim:

1. A method of preparing a compound of formula III:

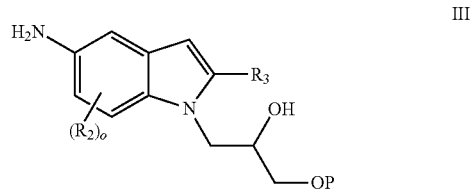

wherein, independently for each occurrence:
R₂ is —R$^J$, —OR$^J$, —N(R$^J$)₂, —NO₂, halogen, —CN, —C₁₋₄haloalkyl, —C₁₋₄haloalkoxy, —C(O)N(R$^J$)₂, —NR$^J$C(O)R$^J$, —SOR$^J$, —SO₂R$^J$, —SO₂N(R$^J$)₂, —NR$^J$SO₂R$^J$, —COR$^J$, —CO₂R$^J$, —NR$^J$SO₂N(R$^J$)₂, —COCOR$^J$;
R$^J$ is hydrogen or C₁₋₆ aliphatic;
R₃ is C₁₋₆ aliphatic optionally substituted with OH, OP, —O—C₁₋₆ aliphatic, aryl, heteroaryl, —O-aryl, or —O-heteroaryl;
P is a protecting group; and
o is an integer from 0 to 3;
comprising the steps of:
a) reacting a compound of formula IIIA:

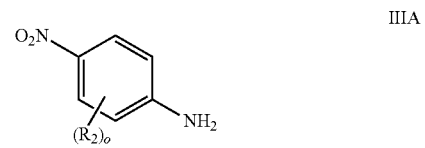

wherein, independently for each occurrence:
R₂ is —R$^J$, —OR$^J$, —N(R$^J$)₂, —NO₂, halogen, —CN, —C₁₋₄haloalkyl, —C₁₋₄haloalkoxy, —C(O)N(R$^J$)₂, —NR$^J$C(O)R$^J$, —SOR$^J$, —SO₂R$^J$, —SO₂N(R$^J$)₂, —NR$^J$SO₂R$^J$, —COR$^J$, —CO₂R$^J$, —NR$^J$SO₂N(R$^J$)₂, —COCOR$^J$;
R$^J$ is hydrogen or C₁₋₆ aliphatic; and
o is an integer from 0 to 3;
with a halogenating reagent in a first organic solvent to form a compound of formula IIIB:

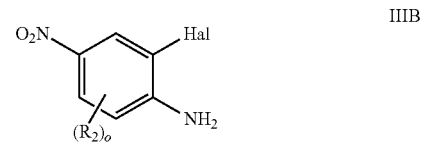

wherein, independently for each occurrence:
R₂ is —R$^J$, —OR$^J$, —N(R$^J$)₂, —NO₂, halogen, —CN, —C₁₋₄haloalkyl, —C₁₋₄haloalkoxy, —C(O)N(R$^J$)₂, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
is an integer from 0 to 3; and
Hal is a halide;
b) reacting the compound of formula IIIB in a second organic solvent with a compound of formula IIIC:

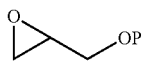
IIIC wherein:
P is a protecting group;
followed by reduction and treatment with acid to form a compound of formula IIID:

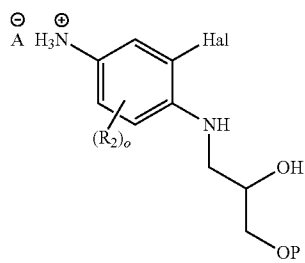
IIID wherein:
R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
o is an integer from 0 to 3;
Hal is a halide;
P is a protecting group; and
A$^\ominus$ is an anion;
c) neutralizing a compound of formula IIID in the presence of a base to form a compound of formula IIID-a:

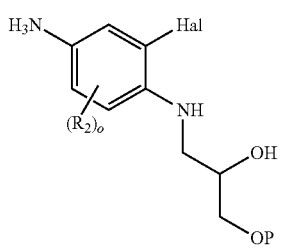
IIID-a wherein:
R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
R$^J$ is hydrogen or C$_{1-6}$ aliphatic;
o is an integer from 0 to 3;

Hal is a halide; and
P is a protecting group;
d) reacting a compound of formula IIID-a in a third organic solvent with a compound of formula IIIE:

IIIE wherein, independently for each occurrence:
R$_3$ is a C$_{1-6}$ aliphatic optionally substituted with OH, OP, —O—C$_{1-6}$ aliphatic, aryl, heteroaryl, —O-aryl, or —O-heteroaryl;
in the presence of a catalyst to form a compound of formula III.

2. The method of claim 1, wherein in formula IIIA, o is 1 and R$_2$ is F.

3. The method of claim 1, wherein in step a), the halogenating reagent is N-bromosuccinimide.

4. The method of claim 1, wherein in step a), the first organic solvent is an aprotic solvent.

5. The method of claim 1, wherein in step a), the first organic solvent is ethyl acetate.

6. The method of claim 1, wherein step a) takes place at about 2° C. to 42° C.

7. The method of claim 1, wherein in formula IIIB, o is 1, R$_2$ is F, and Hal is Br.

8. The method of claim 1, wherein in formula IIIC, P is benzyl.

9. The method of claim 1, wherein in step b), the second organic solvent is an aprotic solvent.

10. The method of claim 1, wherein in step b), the second organic solvent is toluene.

11. The method of claim 1, wherein in step b), the reaction with a compound of formula IIIC takes place at about 60° C. to 100° C.

12. The method of claim 1, wherein in step b), reduction is carried out with hydrogen.

13. The method of claim 1, wherein in step b), the acid is p-toluenesulfonic acid.

14. The method of claim 1, wherein in formula IIID, o is 1, R$_2$ is F, Hal is Br, A$^\ominus$ is Tos$^-$, and P is benzyl.

15. The method of claim 1, wherein in formula IIIE, R$_3$ is C(CH$_3$)$_2$CH$_2$O(benzyl).

16. The method of claim 1, wherein in step c) the base is an inorganic base.

17. The method of claim 1, wherein in step d), the third organic solvent is an aprotic solvent.

18. The method of claim 1, wherein in step d), the third organic solvent is acetonitrile.

19. The method of claim 1, wherein step d) takes place at about 60° C. to 100° C.

20. The method of claim 1, wherein in step d), the catalyst is a palladium catalyst.

21. The method of claim 1, wherein in step d), the catalyst is selected from palladium(II)acetate, Pd(dppf)Cl$_2$, Pd(dba)$_2$, tetrakis(triphenylphosphine)palladium(0), (MeCN)$_2$PdCl$_2$, or tris(dibenzylideneacetone)dipalladium (0).

22. The method of claim 1, wherein in step d), the catalyst is palladium(II)acetate.

23. A compound of formula III:

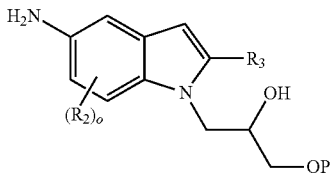

III or a salt thereof,
wherein, independently for each occurrence:

$R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, or —$COCOR^J$;

$R^J$ is hydrogen or $C_{1-6}$ aliphatic;

$R_3$ is $C_{1-6}$ aliphatic optionally substituted with OH, OP, —O—$C_{1-6}$ aliphatic, aryl, heteroaryl, —O-aryl, or —O-heteroaryl;

P is a protecting group; and
o is an integer from 0 to 3.

24. The compound or salt of claim 23, wherein o is 1 and $R_2$ is F.

25. The compound or salt of claim 23, wherein $R_3$ is $C(CH_3)_2CH_2O$(benzyl).

26. The compound or salt of claim 23, wherein P is acetyl, benzoyl, benzyl, methoxyethoxymethyl, dimethoxytrityl, methoxymethyl, methoxytrityl, p-methoxybenzyl, pivaloyl, tetrahydropyranyl, trityl, or trimethylsilyl.

27. The compound or salt of claim 26, wherein P is benzyl.

28. The compound or salt of claim 23, wherein the compound is

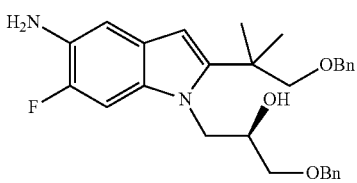 or a salt thereof.

* * * * *

UNITED STATES PATENT AND TRADEMARK OFFICE
CERTIFICATE OF CORRECTION

PATENT NO. : 10,071,979 B2
APPLICATION NO. : 14/687286
DATED : September 11, 2018
INVENTOR(S) : Gerald J. Tanoury et al.

Page 1 of 1

It is certified that error appears in the above-identified patent and that said Letters Patent is hereby corrected as shown below:

In the Claims

Claim 1, Column 61, Line 4, "is an integer from 0 to 3; and" should read --o is an integer from 0 to 3--.

Claim 1, Column 61, Lines 48-56, formula IIID-a,

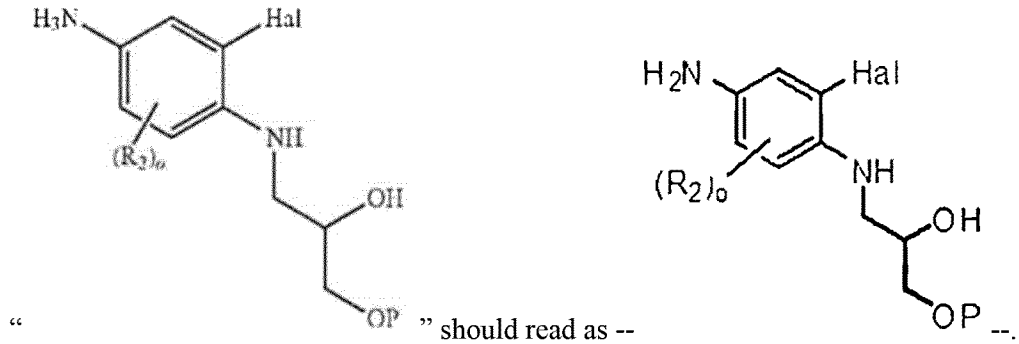

Signed and Sealed this
Fourth Day of December, 2018

Andrei Iancu
*Director of the United States Patent and Trademark Office*